United States Patent
Otsuka et al.

(10) Patent No.: US 12,315,164 B2
(45) Date of Patent: May 27, 2025

(54) IMAGE PROCESSING DEVICE, IMAGE PROCESSING METHOD, AND STORAGE MEDIUM

(71) Applicant: CASIO COMPUTER CO., LTD., Tokyo (JP)

(72) Inventors: Toshihiko Otsuka, Tokyo (JP); Takahiro Tomida, Tokyo (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 409 days.

(21) Appl. No.: 17/762,258

(22) PCT Filed: Sep. 23, 2020

(86) PCT No.: PCT/JP2020/035722
§ 371 (c)(1),
(2) Date: Mar. 21, 2022

(87) PCT Pub. No.: WO2021/060250
PCT Pub. Date: Apr. 1, 2021

(65) Prior Publication Data
US 2022/0343506 A1    Oct. 27, 2022

(30) Foreign Application Priority Data
Sep. 24, 2019    (JP) .................................. 2019-173461

(51) Int. Cl.
*G06T 7/00*    (2017.01)
*G06T 7/246*    (2017.01)

(52) U.S. Cl.
CPC ............ *G06T 7/0016* (2013.01); *G06T 7/246* (2017.01); *G06T 2207/30201* (2013.01)

(58) Field of Classification Search
CPC ................... G06T 7/0016; G06T 7/246; G06T 2207/30201; G06T 7/00; G06T 7/20;
(Continued)

(56) References Cited

U.S. PATENT DOCUMENTS 9,977,875 B2 *    5/2018    Lo .............................. G06T 7/60
10,361,004 B2 *    7/2019    Pai ........................ A61B 5/0075
(Continued)

FOREIGN PATENT DOCUMENTS

| JP | 2005242567 A | 9/2005 | |
| JP | 2012152389 A | 8/2012 | |
| JP | 2016101365 A | 6/2016 | |
| WO | WO-2013104015 A1 * | 7/2013 | ........... G06T 7/0014 |

OTHER PUBLICATIONS

International Search Report (ISR) (and English language translation thereof) dated Nov. 17, 2020, issued in International Application No. PCT/JP2020/035722.
(Continued)

*Primary Examiner* — Ping Y Hsieh
*Assistant Examiner* — Vaisali Rao Koppolu
(74) *Attorney, Agent, or Firm* — Holtz, Holtz & Volek PC

(57) ABSTRACT

An image processing device includes an input/output interface, and at least one processor. The at least one processor executes: detecting feature points in a facial image of an object included in an image taken from the input/output interface; acquiring first distance information between the feature points before a beauty treatment is performed; acquiring second distance information between the feature points at a second timing after the beauty treatment is performed; acquiring a difference value between the first distance information and the second distance information; and determining whether the beauty treatment is correctly given or has been given based on a different value between the acquired distance information.

17 Claims, 20 Drawing Sheets

(58) Field of Classification Search
CPC .... A61H 2201/0157; A61H 2201/0188; A61H 2201/1253; A61H 2201/5015; A61H 2201/5043; A61H 2201/5048; A61H 2201/5092; A61H 2205/022; A61H 2230/855; A61H 7/007; A61B 5/1072; A61B 5/1079; A61B 5/4848; A61B 5/4887; A61B 5/743; A61B 5/744; A61B 5/0022; A61B 5/021; A61B 5/024; A61B 5/026; G16H 20/70; G16H 30/20; G16H 30/40; G16H 40/67; G06V 40/171; A45D 44/00

See application file for complete search history.

(56) References Cited

U.S. PATENT DOCUMENTS

| | | | | |
|---|---|---|---|---|
| 2005/0201594 | A1* | 9/2005 | Mori | A61B 5/1128 |
| | | | | 348/136 |
| 2016/0154992 | A1* | 6/2016 | Shinoda | A61B 5/442 |
| | | | | 382/103 |
| 2017/0319065 | A1* | 11/2017 | Kimura | A61B 5/0077 |
| 2020/0146622 | A1* | 5/2020 | Bock | G06V 40/161 |

OTHER PUBLICATIONS

Written Opinion dated Nov. 17, 2020, issued in International Application No. PCT/JP2020/035722.

* cited by examiner

LEG ROTATES ABOUT
HINGES TO ALLOW DEVICE
TO BE FREESTANDING

IMAGE PROCESSING DEVICE, IMAGE PROCESSING METHOD, AND STORAGE MEDIUM

TECHNICAL FIELD

The present invention relates to an image processing device, an image processing method, and a storage medium.

BACKGROUND ART

For determination of whether a facial massage is correctly given during a beauty treatment, it is required to measure the position of the face and how hard the face is pressed with fingers or hands. In this case, pressure information and positional information need to be acquired from sensors or markers attached to the fingers or the hands. This requires a complicated system. Image recognition using a camera cannot clearly distinguish the fingers and the hands from the color of the face, and thus, has difficulty in increasing the accuracy of pieces of information including the positional information.

Japanese Unexamined Patent Application Publication No. 2012-152389 discloses an appliance equipped with a mirror. This appliance can extract feature points defining the degree of fatigue of a user from a facial image using a feature extraction unit, and can show information about the degree of fatigue calculated from the feature points on the mirror.

An image processing device according to an aspect of the present invention includes an input/output interface, and at least one processor. The at least one processor executes: detecting feature points in a facial image of an object included in an image taken from the input/output interface; acquiring first distance information between the feature points before a beauty treatment is performed; acquiring second distance information between the feature points at a second timing after the beauty treatment is performed; acquiring a difference value between the first distance information and the second distance information; and determining whether the beauty treatment is correctly given or has been given based on a different value between the acquired distance information.

BRIEF DESCRIPTION OF THE DRAWINGS

FIG. 130 is a flowchart of operation of the image processing device according to the embodiment of the present invention;

PREFERRED MODE FOR CARRYING OUT THE INVENTION

Embodiments of the present invention will be described below with reference to the drawings.

[Outline of Embodiment]

An image processing device 1 according to an embodiment of the present invention is a smart mirror constituted as a portable and freestanding mirror. The image processing device 1 takes an image of a user who is an object seeing the mirror. Based on the image taken of the user, particularly an image taken of a face of the user, the image processing device 1 detects feature points from the user's face, and continuously takes the image of the user's face to track the movement of the feature points. The image processing device 1 compares a locus obtained as a result of the tracking with preset locus information to output whether a beauty treatment is correctly performed by the user during the beauty treatment, and the effect of the treatment.

[System Configuration]

Figure 1:
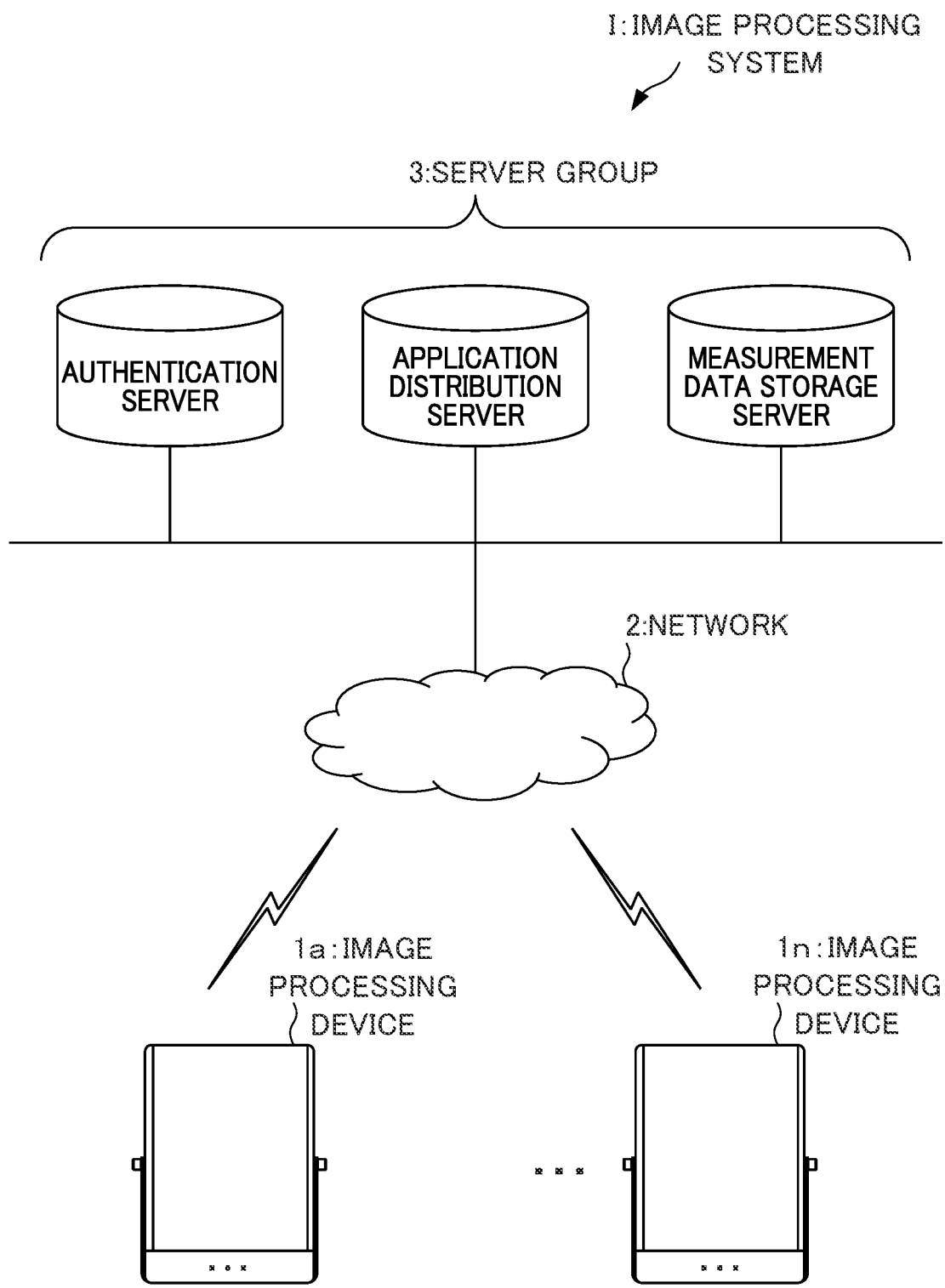
FIG. 1 is a diagram illustrating a configuration of an image processing system according to an embodiment of the present invention.

FIG. 1 is a block diagram illustrating an overall configuration of an image processing system I including the image processing device 1 of the present embodiment. As shown in FIG. 1, the image processing system I includes a plurality of image processing devices 1, a network 2, and a server group 3. The number of image processing devices 1 is not limited to particular values. The image processing system I may include n (n is any natural number) image processing devices 1. In the following description, the n image processing devices 1 will be simply, referred to as the "image processing device 1" without adding a letter of the alphabet to the reference numeral when no distinction between the n image processing devices 1 is required.

The image processing device 1 detects the feature points of the user from an image, tracks the movement of the feature points detected, compares the locus obtained as a result of the tracking with the preset locus information, and displays the comparison result. The image processing device 1 is connected to servers included in the server group 3 via the network 2 to be able to mutually communicate with the servers.

The network 2 is achieved, for example, by any one of the Internet, a local area network (LAN), or a mobile telephone network, or a combination of them.

The server group 3 includes various servers that cooperate with the image processing device 1. For example, the server group 3 includes an authentication server that authenticates the user of the image processing device 1. For example, the server group 3 also includes an application distribution server that achieves one of functions of the image processing device 1. For example, the server group 3 further includes a measurement data storage server that stores user profile information, which is information including setting information related to the user, and a history of usage of the image processing device 1 by the user.

The image processing system I shown in FIG. 1 is merely an example. The server group 3 may include a server having a different function. The servers included in the server group 3 may be formed as independent server devices, or a single server device.

[Configuration of Appearance]

Figure 2:
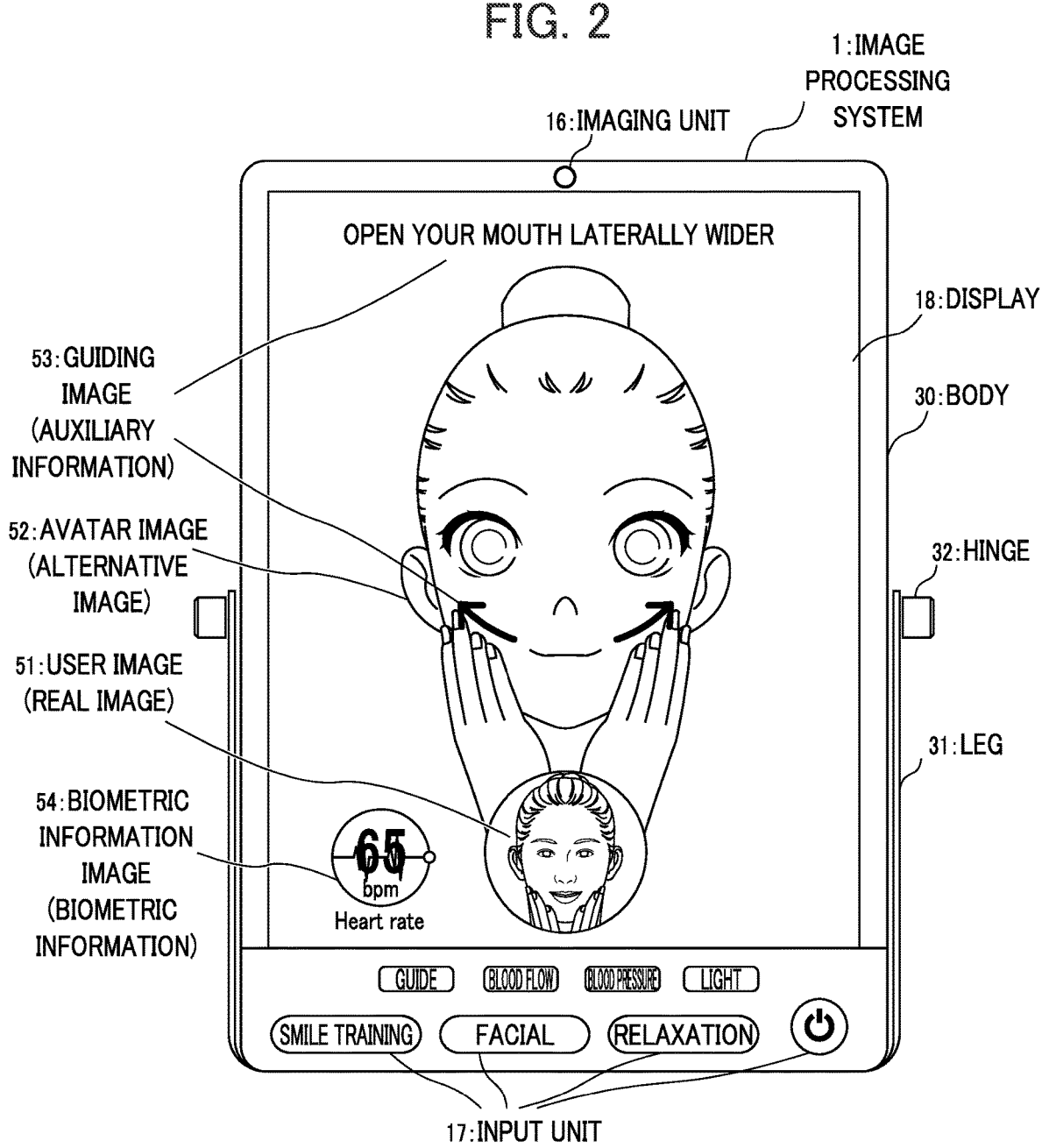
FIG. 2 is a diagram illustrating an appearance of an image processing device according to an embodiment of the present invention as viewed from the front.

FIG. 2 is a diagram illustrating an appearance of the image processing device 1 according to the embodiment of the present invention as viewed from the front. FIG. 3 is a diagram illustrating an appearance of the image processing device 1 as viewed from the side. A front surface of the image processing device 1 has a size of A4 defined by an international standard, e.g., International Organization for Standardization (ISO) 216.

As shown in FIGS. 2 and 3, the image processing device 1 includes a body 30, a leg 31, and hinges 32. The body 30 is a portion including a display 18 and other pieces of hardware which will be described later with reference to FIG. 4. The leg 31 and the hinges 32 are members that allow the image processing device 1 to be freestanding. The leg 31 is supported by the hinges 32 to be rotatable with respect to the body 30.

Figure 3A:
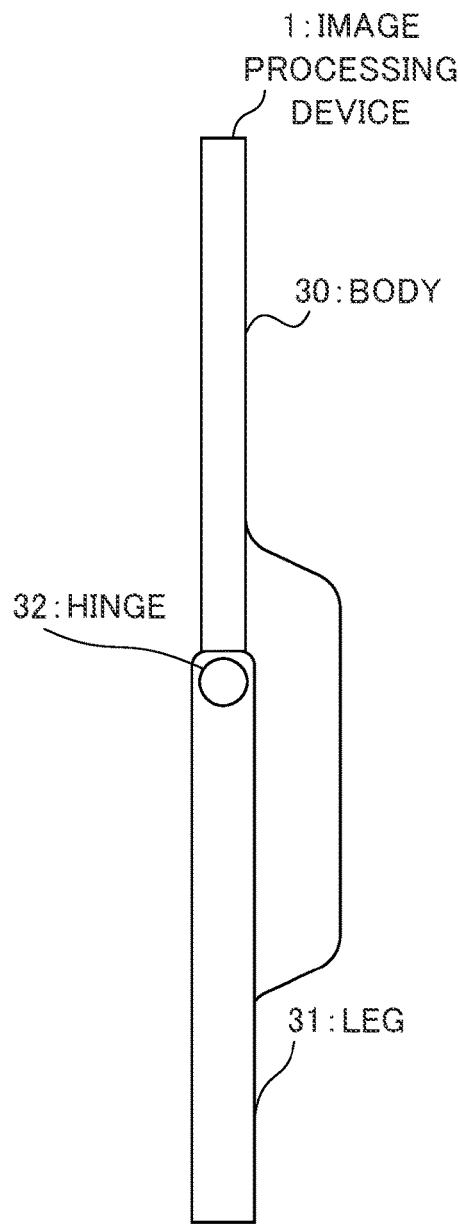
FIGS. 3A and 3B are diagrams illustrating an appearance of the image processing device according to the embodiment of the present invention as viewed from the side.
Figure 3B:
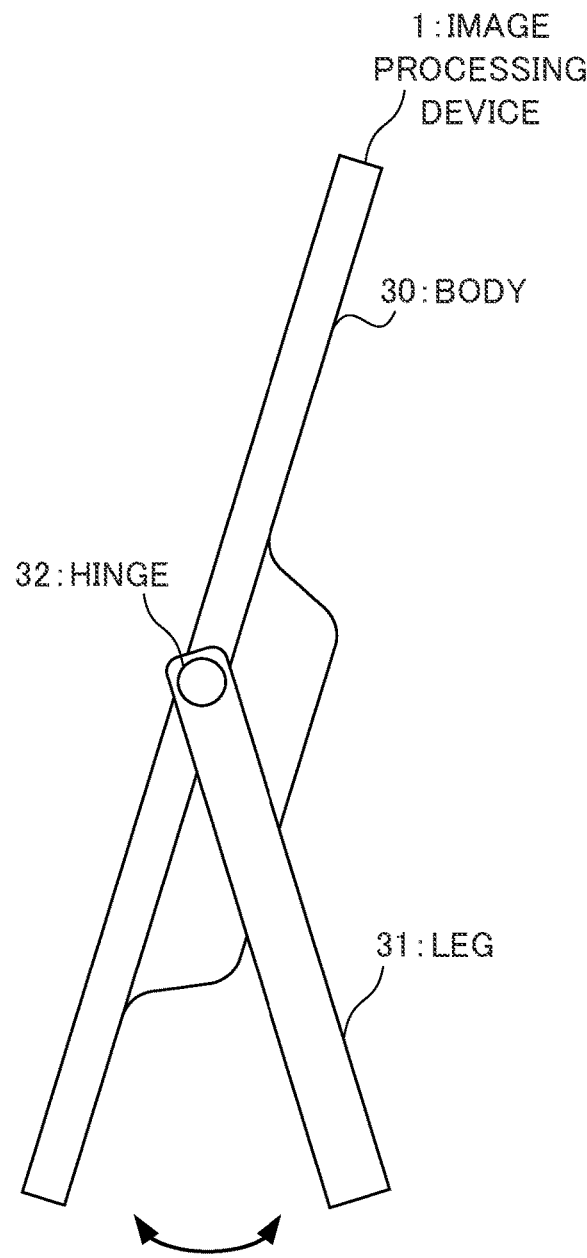

As shown in FIG. 3A, when carrying the image processing device 1, the user can align the side surface of the body 30 with the side surface of the leg 31 to reduce the size of the image processing device 1. When using the image processing device 1 on a desk, the user rotates the leg 31 about the hinges 32 so that the image processing device 1 can be freestanding as shown in FIG. 3B. The hinges 32 have a mechanism for holding the leg 31 at a predetermined angle so that the image processing device 1 can be freestanding.

The body 30 includes the display 18 as described above. The display 18 is a portion on which various types of information are shown to the user. The display 18 shows, for example, a user image which is a real image of the user, who is a subject, taken by an imaging unit 16 (corresponding to a user image 51 in the drawing), an avatar image which is an alternative image of the user (corresponding to an avatar image 52 in the drawing), a guiding image which is auxiliary information for giving guidance (corresponding to a guiding image 53 in the drawing), and a biometric information image indicating biometric information of the user (corresponding to a biometric information image 54 in the drawing). In this case, the display 18 shows t-e guiding image combined with, and superposed on, the avatar image.

The user seeing the display 18 can recognize various types of information at a time. As described above, those shown on the display 18 have a sense of unity suitable for the user to see, with no discomfort in how they look.

As shown in FIG. 2, the image processing device 1 further includes an imaging unit 16, an input unit 17, and the display 18 as components forming the appearance.

The imaging unit 16 is a portion that takes an image of a subject, i.e., the user who faces the display 18 when using the image processing device 1. The imaging unit 16 is positioned to be able to take an image of the face of the user in front of the display 18. For example, the imaging unit 16 is arranged on the front surface of the body 30 above the display 18 as shown in the drawing.

The input unit 17 is a portion that accepts input from the user. The input unit 17 includes, for example, a plurality of buttons. The drawing shows, as examples, switching buttons used for switching among various modes, such as a face-slimming massage, smile training, and recording of biometric information, and a button for turning the power of the image processing device 1 on/off.

The components forming the appearance of the image processing device 1 are described above. Note that the components are merely examples, and are not limited to these examples.

For example, the image processing device 1 may further include a light emitter that illuminates the user facing the display 18. When the light emitter throws light having adjusted illuminance and color components on the user, the image processing device 1 functions as an illuminated mirror. The image processing device 1 may have two or more light emitters. The light emitter may be arranged above or below the display 18, or may surround the display 18.

The number and position of the input unit 17 may be changed. For example, part of the display 18 may be formed as a touch screen so that the input unit 17 and the display 18 are incorporated into a single unit.

[Hardware Configuration]

Figure 4:
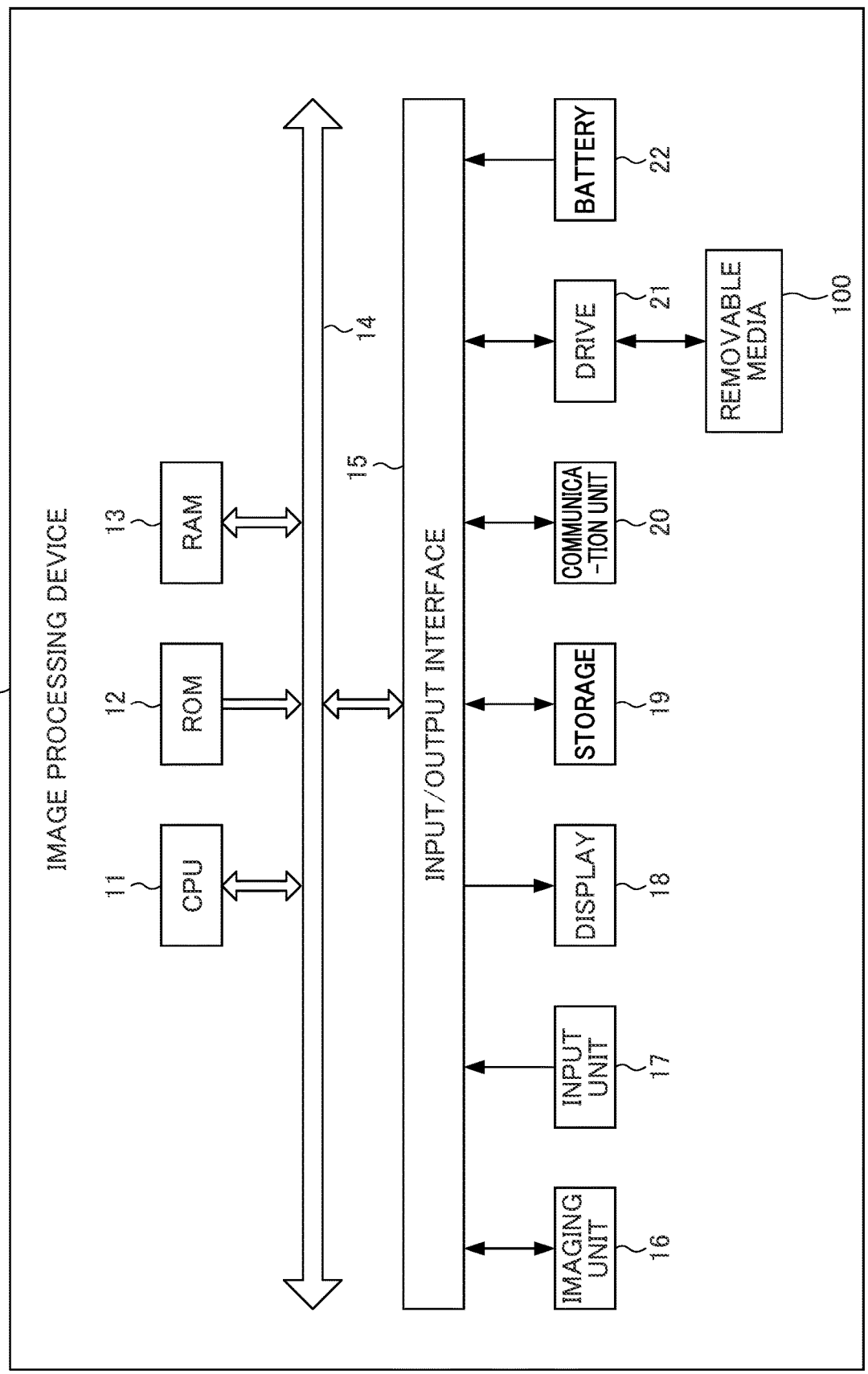
FIG. 4 is a block diagram illustrating a configuration of hardware of the image processing device according to the embodiment of the present invention.

FIG. 4 is a block diagram illustrating a configuration of hardware of the image processing device 1. As shown in FIG. 4, the image processing device 1 includes a central processing unit (CPU) 11 which is a processor, a read only memory (ROM) 12, a random access memory (RAM) 13, a bus 14, an input/output interface 15, the imaging unit 16, the input unit 17, the display 18, a storage 19, a communication unit 20, a drive 21, and a battery 22.

The CPU 11 executes various types of processing in accordance with programs stored in the ROM 12 or loaded from the storage 19 to the RAM 13.

The RAM 13 also stores data required for the CPU 11 to execute various types of processing as appropriate.

The bus 14 mutually connects the CPU 11, the ROM 12, and the RAM 13. The input/output, interface 15 is also connected to the bus 14. The input/output interface 15 is connected to the imaging unit 16, the input unit 17, the display 18, the storage 19, the communication unit 20, the drive 21, and the battery 22.

Although not shown, the imaging unit 16 includes an optical lens and an image sensor. The optical lens is comprised of a lens that gathers light, such as a focus lens and a zoom lens, for taking an image of a subject. The focus lens forms an image of the subject on a photosensitive surface of the image sensor. The zoom lens freely changes a focal length in a certain range. The imaging unit 16 further includes a peripheral circuit that adjusts setting parameters, such as a focal point, exposure, and white balance, as needed.

The image sensor is comprised of, for example, a photoelectric conversion element and an analog front end (APE). The photoelectric conversion element includes, for example, a complementary metal oxide semiconductor (CMOS). An image of the subject enters the photoelectric conversion element from the optical lens. The photoelectric conversion element photoelectrically converts the image of the subject (takes the image), accumulates an image signal for a certain period of time, and then successively supplies the accumulated image signal as an analog signal to the AFE. The AFE executes various types of signal processing, such as analog/digital (A/D) conversion processing, on the analog signal. A digital signal is generated by the various types of signal processing, and outputted as an output signal of the imaging unit 16. The output signal of the imaging unit 16 is suitably supplied to the components, such as the CPU 11.

The input unit 17 includes various buttons and a microphone, and enters various types of information in response to an instruction by the user's operation or voice.

The display 18 is comprised of a liquid crystal display, and shows an image corresponding to the image data outputted by the CPU 11.

The storage 19 is comprised of a semiconductor memory, such as dynamic random access memory (DRAM), and stores various types of data.

The communication unit 20 performs communication control so that the CPU 11 communicates with other devices (e.g., the servers included in the server group 3) via the network 2.

The drive 21 is comprised of an interface that can accept a removable media 100. The drive 21 suitably accepts the removable media 100, such as a magnetic disc, an optical disc, a magneto-optical disc, or a semiconductor memory. The removable media 100 stores programs for executing composite display processing which will be described later, and various data including the image data. The programs and various data such as the image data read from the removable media 100 by the drive 21 are stored in the storage 19 as needed.

The battery 22 supplies power to the components, and is chargeable when connected to an external power supply. When the image processing device 1 is not connected to the external power supply, the power from the battery 22 operates the image processing device 1.

The image processing device 1 may further include other pieces of hardware in addition to the above-described ones. For example, the image processing device 1 may include a lamp, a speaker, or a vibration motor, and may further include an output unit that outputs light, sound, or a vibration signal.

[Functional Configuration]

Figure 5:
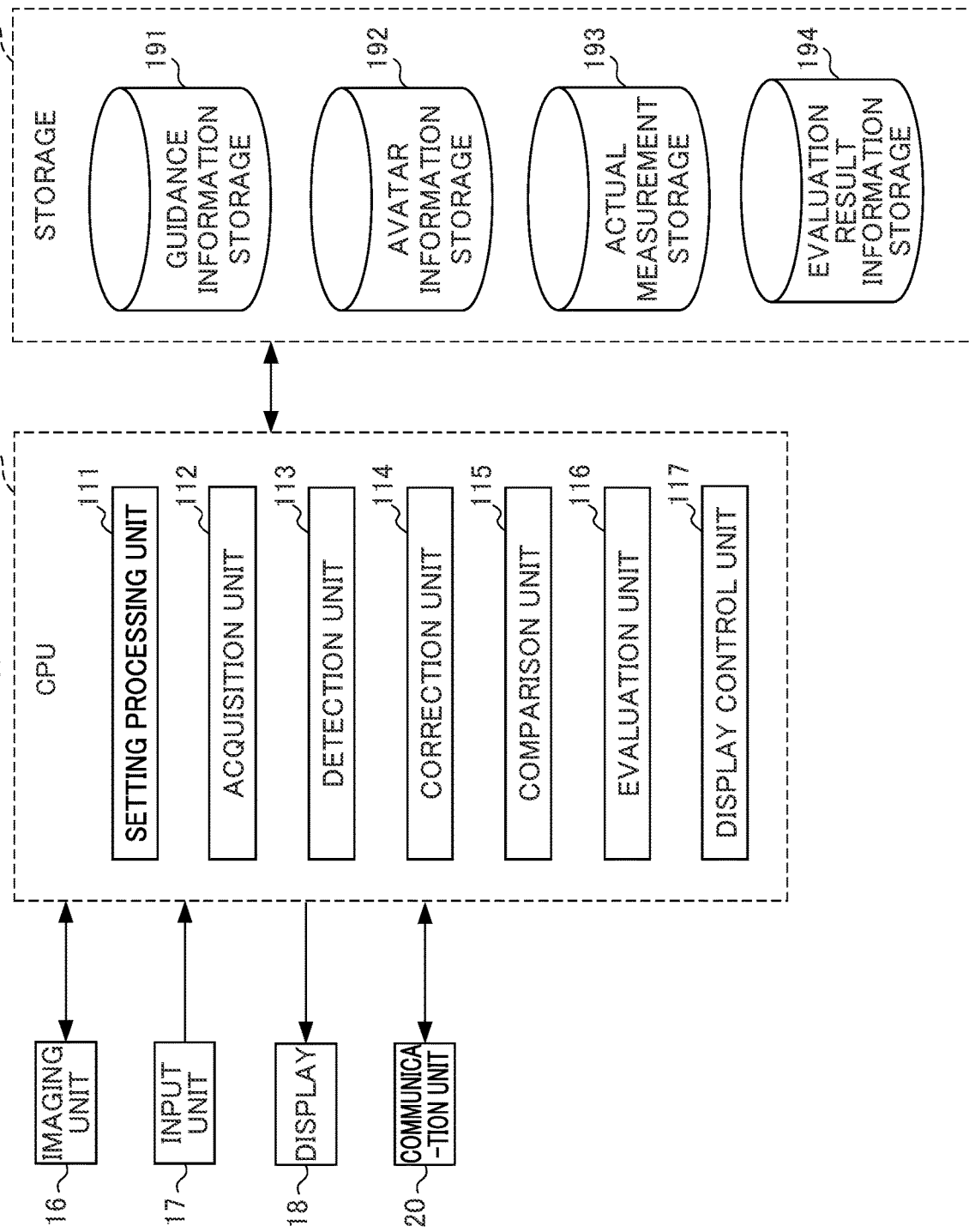
FIG. 5 is a functional block diagram illustrating one, for executing measurement processing, of functional configurations of the image processing device according to the embodiment of the present invention.

FIG. 5 is a functional block diagram illustrating one, for executing image processing, of functional configurations of the image processing device 1. Image processing is a series of processing executed to display an image based on a change of feature points acquired from the user by the image processing device 1.

The storage 19 that stores various types of information will be described first. As shown in FIG. 5, an area of the storage 19 includes a guidance information storage 191, an avatar information storage 192, an actual measurement information storage 193, and an evaluation result information storage 1944.

The guidance information storage 191 stores various types of data related to guidance in the display processing. For example, the guidance information storage 191 stores guiding image data, text data, and sound data for generating guidance information to be shown in the display processing. In particular, the guidance information storage 191 of the present embodiment stores locus information, which is information about a locus that the feature points are supposed to form during a facial massage given as a beauty treatment. The guidance information storage 191 also stores distance information, which is information about an ideal distance between the feature points. More specifically, the distance information may be information about an ideal distance that varies depending on partial change in shape of a face caused by the massage. The guidance information storage 191 also stores timing information about desirable timing when the movement of the massage changes. The guidance information storage 191 also stores the order of display of many items of guidance information for presenting a series of guidance, a condition for switching the displayed guidance information to next guidance information, and data for generating various user interfaces. The guidance information storage 191 also stores user profile information generated in connection with the display processing. The guiding image may be image data previously generated, or may be generated by computer graphics (CG) in real time based on calculation.

The avatar information storage 192 stores various types of data related to an avatar which is an alternative of a real image of the user. For example, the avatar information storage 192 stores avatar image data for generating an avatar image shown in composite display processing, and a condition for selecting an avatar image to be shown in the guidance. The avatar image may be image data previously generated, or may be generated by CC; in real time based on calculation. The avatar image may be, for example, an image of a character that imitates a human or an animal. Any number of avatar images may be prepared, and a suitable one may be selected depending on the characteristics of the user (e.g., sex, age, and preference of the user) or what the guidance tells. The avatar image may be continuous images for creating animation of a character. Each data may be stored as a single library per type of guidance so that the data is easily read out for creating a series of guidance.

The actual measurement information storage 193 stores pieces of actual measurement information about the feature points detected by a detection unit 113, positions of reference points included in the feature points, and a distance between the feature points calculated by a comparison unit 115. In particular, the actual measurement information storage 193 may store, as the distance information, initial values of coordinates of the feature points including the reference points, and an initial value of the distance between the feature points before the massage as the beauty treatment starts. More specifically, the distance information may be information about a distance that varies depending on partial change in shape of a face caused by the massage.

The evaluation result information storage 194 stores information that an evaluation unit 116 uses to generate evaluation result information based on a result of comparison between the result of tracking of the movement of the feature points and the preset locus information by the comparison unit 115, information for displaying the evaluation result, and information indicating the evaluation result. Evaluation processing the evaluation unit 116 will be described later.

The pieces of information stored in the guidance information storage 191, the avatar information storage 192, the actual measurement information storage 193, and the evaluation result information storage 194 may be stored in the storage 19 only, or may be suitably stored in the removable media 100 by the drive 21. The pieces of information stored in the guidance information storage 191, the avatar information storage 192, the actual measurement information storage 193, and the evaluation result information storage 194 may be suitably stored in a measurement data storage server included in the server group 3.

Functional blocks for executing the image processing will be described below. As shown in FIG. 5, a setting processing unit 111, an acquisition unit. 112, a detection unit 113, a correction unit 114, a comparison unit. 115, an evaluation unit. 116, and a display control unit 117 function in the CPU 11.

The setting processing unit 111 controls settings related to the image processing and the display processing. The setting processing unit 111 acquires application software for executing the display processing from, for example, the application distribution server included in the server group 3, and runs the application software. The setting processing unit 111 communicates with, for example, the authentication server included in the server group 3, to authenticate the user who performs the display processing. The setting processing unit 111 communicates with, for example, the measurement data storage server included in the server group 3, to update the user profile information in the display processing.

The setting processing unit 111 displays a menu for presenting the guidance based on the application software for executing the display processing. For example, the setting processing unit 111 displays a menu including options to choose the contents of the guidance, such as "face-slimming massage", "smile training", "measurement of biometric information", and "makeup". The setting processing unit 111 receives an entry of the contents of guidance chosen by the user who referred to the menu via the input unit 17. For example, the setting processing unit 111 receives that the "face-slimming massage" is chosen. Then, the display processing is executed to provide the guidance about the face-slimming massage. The face-slimming massage is a massage given to the user's face by the user, such as a lymphatic massage that reduces the swelling of the face by lymphatic drainage.

The acquisition unit 112 acquires an image of an object taken by the imaging unit 16. In the present embodiment, the "object" is preferably, but not limited to, an organ of a human, particularly a face of a human.

The detection unit 113 detects the feature points in a real image included in the image of the object acquired by the acquisition unit 112. In the present embodiment, the "image of the object" is an image including the object itself and its background, and indicates an imaging range (imaging angle of view) of the imaging unit 16. The "real image" is the object itself (or an area of the image indicating the object). Especially in the present embodiment, the "image of the object" is suitably an image including an image of a human's face, and the "real image of the object" is suitably a real image of the human's face, but these images are not limited to such examples.

The "feature points" are points (or areas) provided to detect and recognize the shape of organs (eyebrows, eyes, nose, mouth, facial contour) in the image of the user's face.

Figure 6:
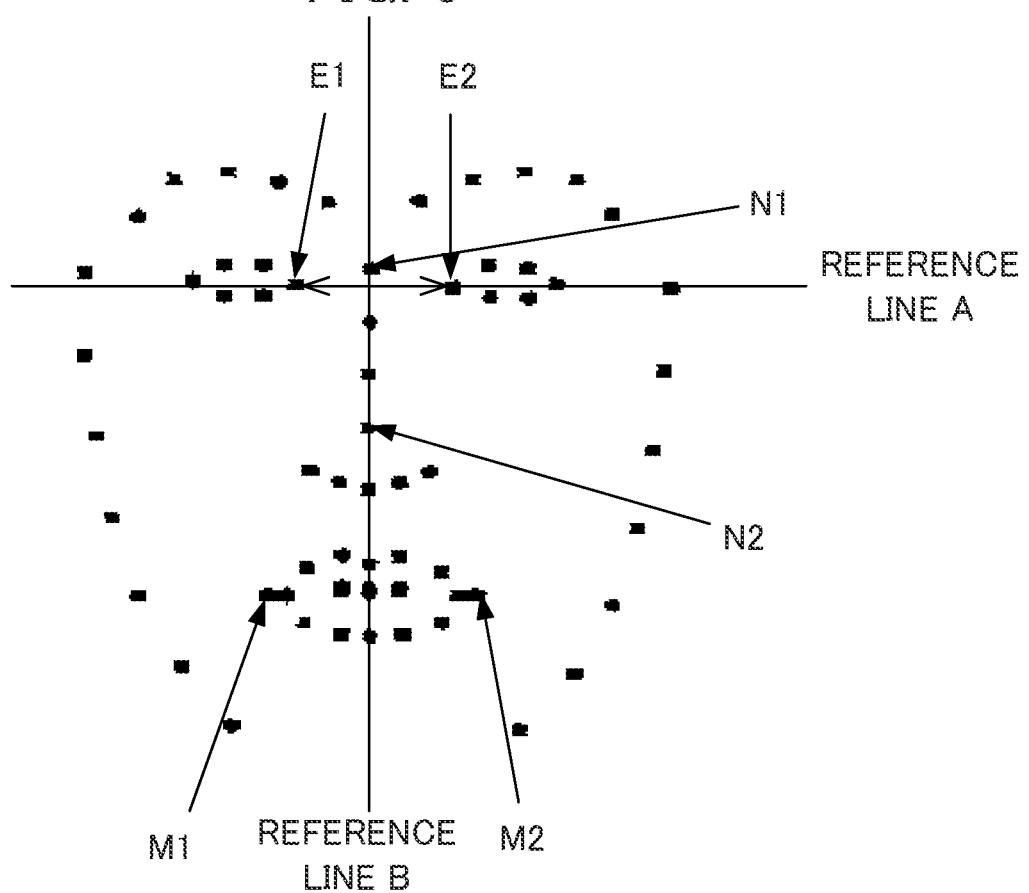
FIG. 6 is a diagram illustrating an example of feature points, reference points, and reference lines detected by the image processing device according to the embodiment of the present invention.

FIG. 6 shows an example of the feature points, in particular, the reference points and reference lines which are used as a reference for the detection of the movement of the feature points. As shown in FIG. 6, the feature points are arranged along the contour of the eyes, along the dorsum and wings of the nose, around the mouth, and along the eyebrows and the contour of the cheeks extending from the eyebrows. Among the feature points, two at the inner corners of the eyes (E1 and E2 in FIG. 6) and two at the corners of the mouth (M1 and M2 in FIG. 6) are possible reference points. A straight line connecting E1 and E2 (reference line A) and a straight line connecting N1 and N2 (reference line B) are possible reference lines. A distance between E1 and E2 is the distance information described above. When the beauty treatment, e.g., a massage, changes the distance between E1 and E2, the changed distance is compared with the distance information initially set.

Figure 7:
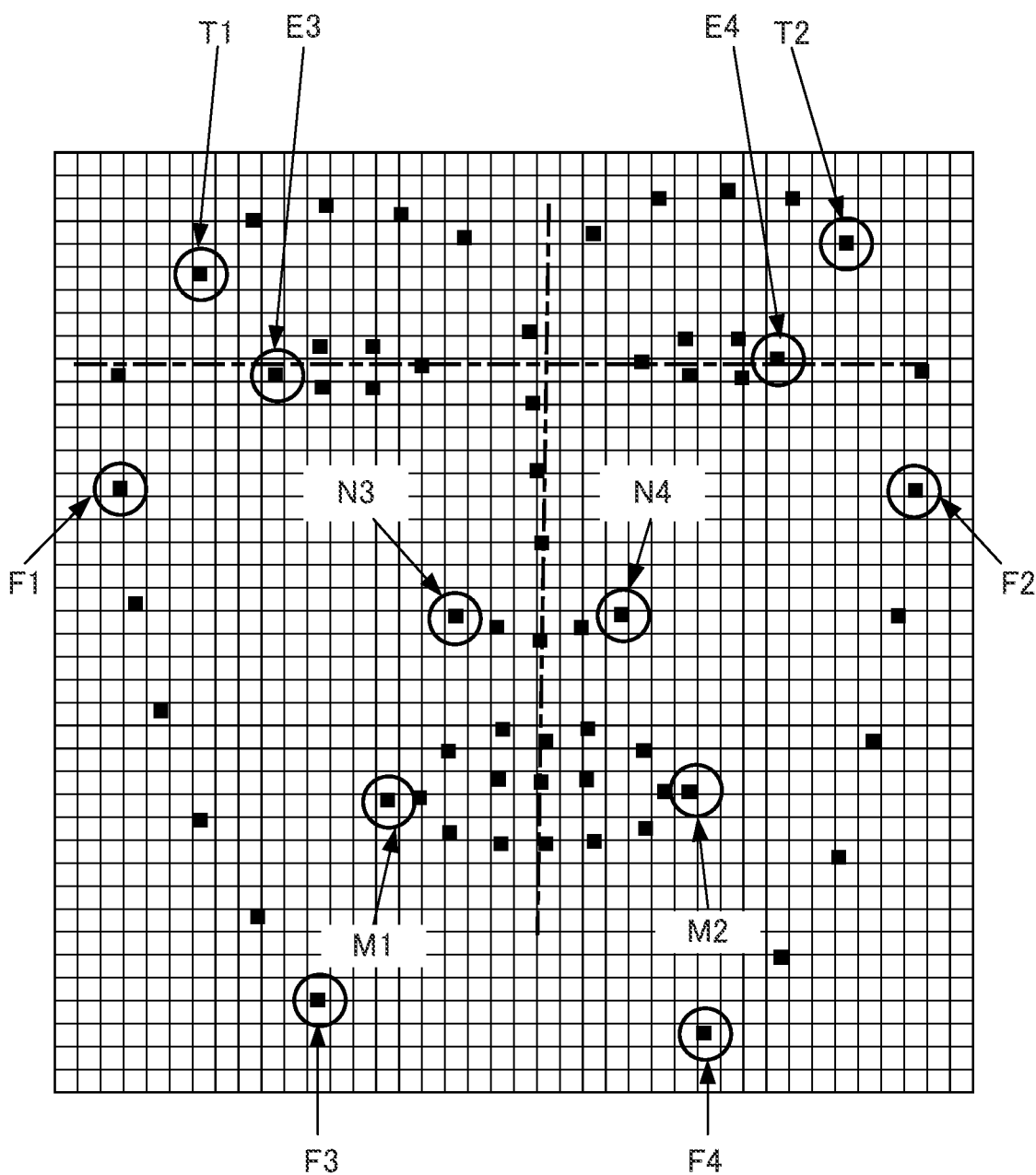
FIG. 7 is a diagram illustrating examples of reference points and reference lines used for different treatments according to the embodiment of the present invention.

FIG. 7 shows examples of the reference points and the reference lines used for different treatments. For a massage around the eyes, the feature points corresponding to two outer corners of the eyes enclosed in circles in FIG. 7 (E3 and E4) will be the reference points.

For a massage of the temple, the feature points corresponding to two ends of the eyebrows enclosed in circles in FIG. 7 (T1 and T2) will be the reference points.

For a massage around the nose, the two feature points corresponding to the ends of the nasal wings of the nose enclosed in circles in FIG. 7 (N3 and N4) will be the reference points.

For a massage of the cheeks and the periphery of the mouth, the two feature points corresponding to the corners of the mouth enclosed in circles in FIG. 7 (M1 and M2) will be the reference points.

For a massage of the whole face, the uppermost two of the feature points along the contour of the cheeks enclosed in circles in A. 7 (F1 and F2) and the lowermost two of the feature points along the contour of the cheeks enclosed in circles in FIG. 7 (F3 and F4) will be the reference points.

Figure 8A:
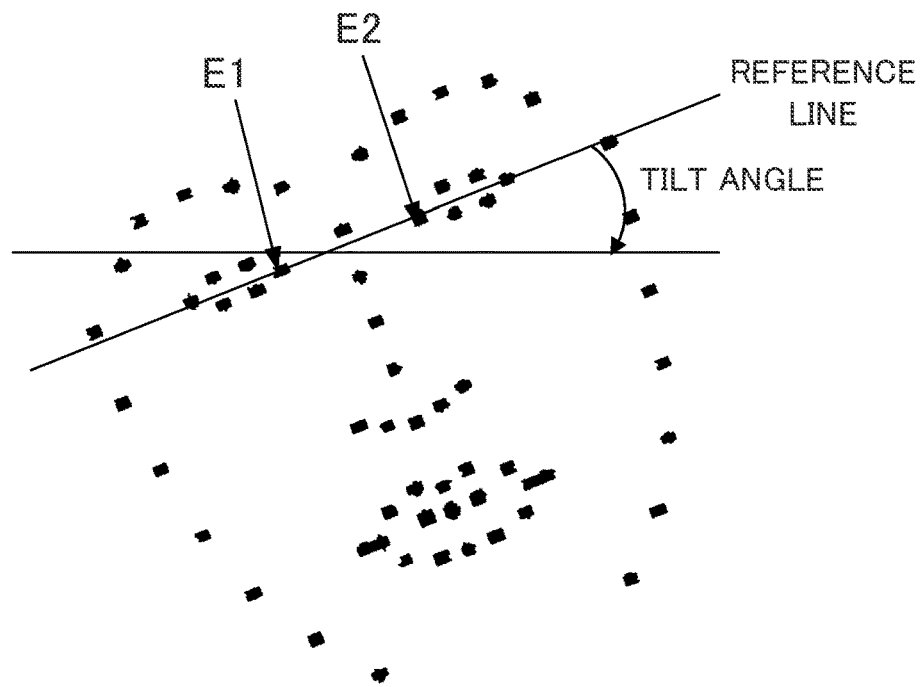
FIG. 8A is a diagram illustrating how a correction is made according to the embodiment of the present invention.
Figure 8B:
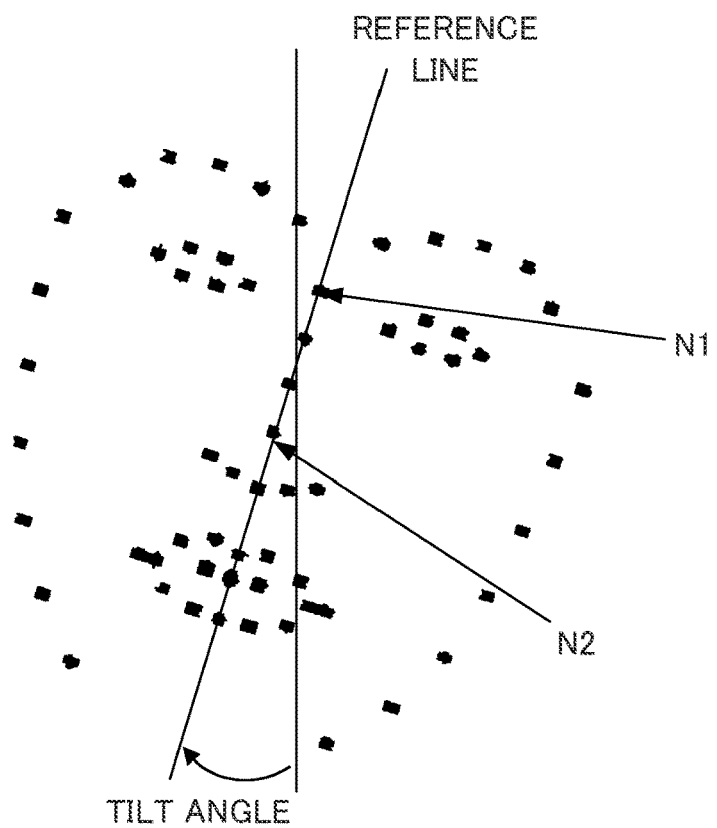
FIG. 8B is a diagram illustrating how a correction is made according to the embodiment of the present invention.

The correction unit 114 performs scaling of the taken real image, for example, when the user's face (real image) taken by the imaging unit 16 is inclined at a predetermined angle of rotation, or depending on the distance between the imaging unit 16 and the user's face. More specifically, the correction unit 114 corrects the positional relationship among the plurality of feature points detected by the detection unit 113. FIGS. 8A and 8B show how the correction is made by the correction unit 114. For correction of the tilt of a horizontal line, an angle formed by the reference line connecting E1 and E2 and a horizontal straight line is detected as shown in FIG. 8A, and the image is rotated to reduce the angle to zero. For correction of the tilt of a vertical line, an angle formed by the reference line connecting N1 and N2 and a vertical straight line is detected as shown in FIG. 8B, and the image is rotated to reduce the angle to zero. For correction of the size of the image, the image is magnified or reduced so that the distance between E1 and E2 becomes a preset reference distance.

The comparison unit 115 tracks the movement of the feature points detected by the imaging unit 16 continuously taking the image of the object, and compares a locus obtained as a result of the tracking with preset locus information. The comparison unit 115 may compare the timing of the movement with preset timing information.

The comparison unit 115 may obtain a distance between the feature points detected, and compare the distance with the preset distance information. For example, the comparison unit 115 may compare the distance between the reference point and the reference line with the preset distance information.

FIGS. 9A to 12B show examples of the distance between the reference point and the reference line and the preset distance information, which are compared by the comparison unit 115.

Figure 9A:
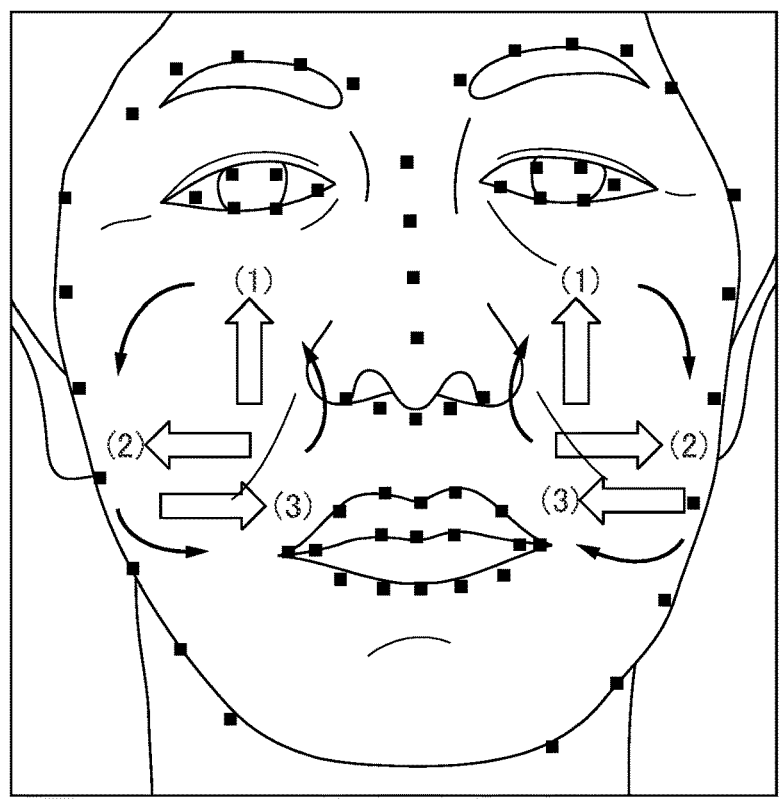
FIGS. 9A and 9B are diagrams illustrating an example of a distance between a reference point and a reference line and preset distance information according to the embodiment of the present invention.

FIG. 9A shows an example of the movement of fingers giving a massage. In this example, the massage is given to the cheeks and the periphery of the mouth as described with reference to FIG. 7. In this massage, specifically, the user first pushes the cheeks up in the direction (1) with the fingers placed near the mouth, moves the right fingers to the right and the left fingers to the left so that the cheeks spread in the directions (2), and finally moves the fingers in the directions (3) so that the fingers moved to the right and the left return to the original positions while pushing the cheeks toward the center of the face.

Figure 9B:
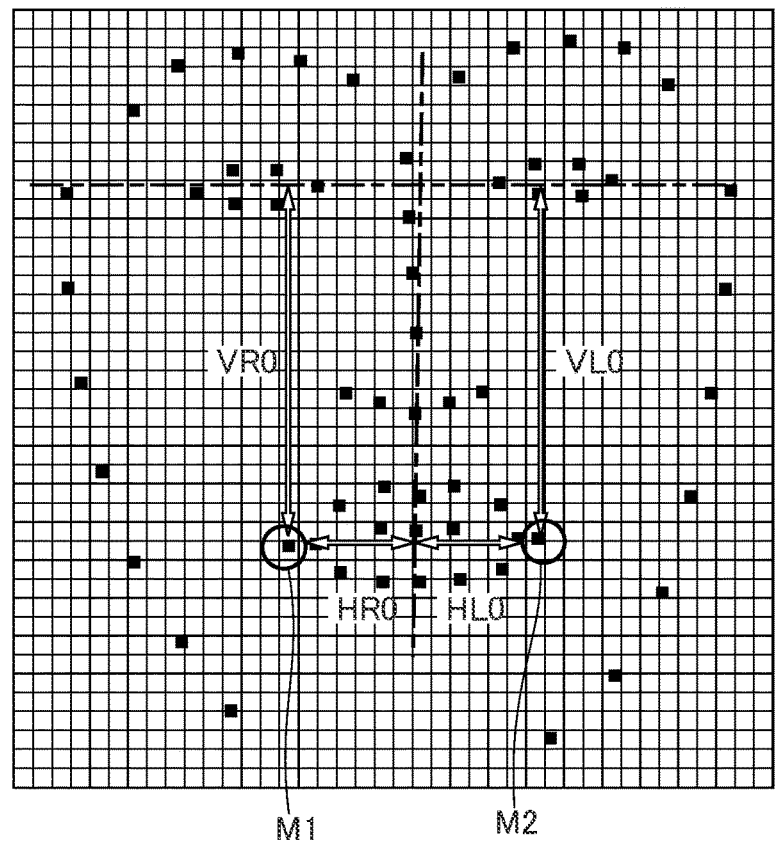

Points M1 and M2 in the real image taken by the imaging unit 16 before giving the massage are set as the reference points as shown in FIG. 9B. A distance from M1 to the reference line connecting the two outer corners of the eyes is referred to as VR0, and a distance from M2 to the same reference line as VL0. A distance from M1 to the reference line passing the dorsum of the nose is referred to as HR0, and a distance from M2 to the same reference line as HL0. The comparison unit 115 stores the pieces of distance information thus defined in the actual measurement information storage 193.

Figure 10A:
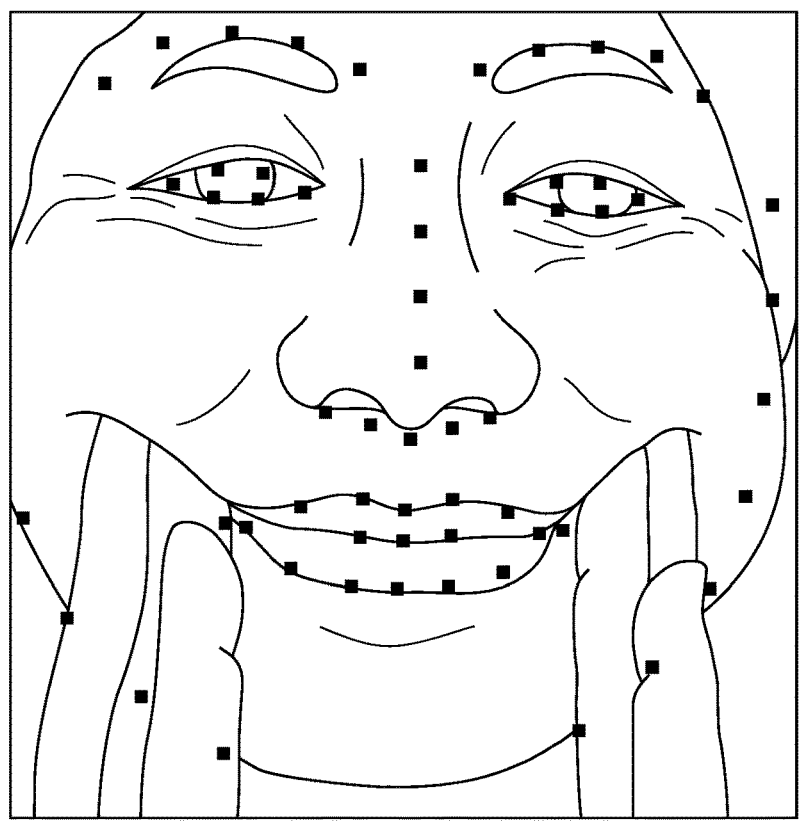
FIGS. 10A and 10B are diagrams illustrating an example of the distance between the reference point and the reference line and the preset distance information according to the embodiment of the present invention.
Figure 10B:
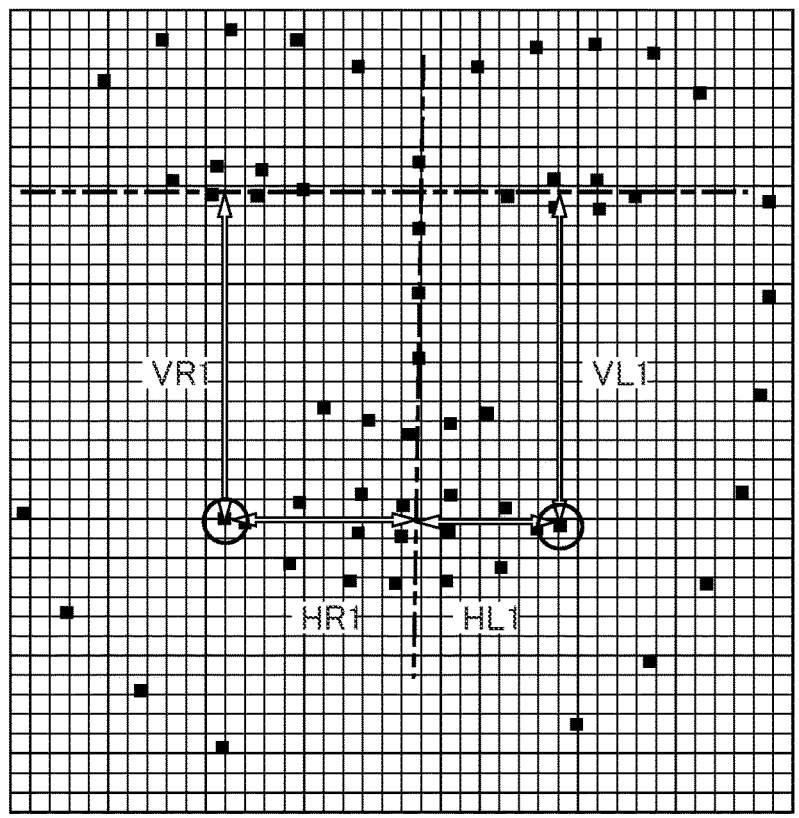

When the massage as the treatment starts, the fingers move in the direction (1) as shown in FIG. 10A. Then, the distances change as shown in FIG. 10B, i.e., VR0 changes to VR1, VL0 to VL1, HR0 to HR1, and HL0 to HL1. The changed distances are compared to the pieces of distance information. In the example shown in FIG. 10B, VR0>VR1, VL0>VL1, HR0≤HR1, and HL0≤HL1 are met.

Figure 11A:
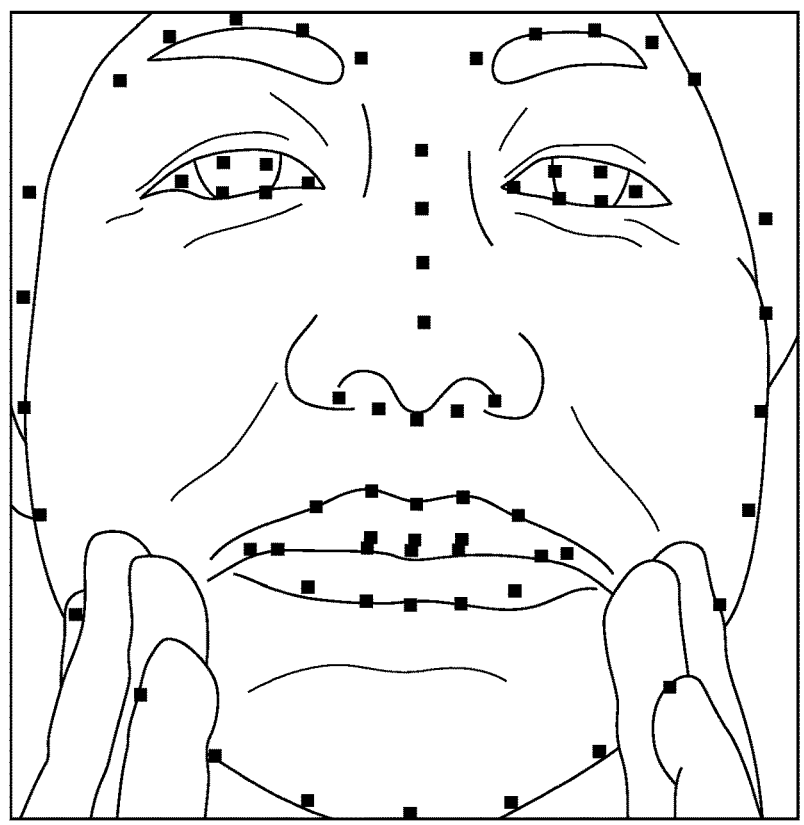
FIGS. 11A and 11B are diagrams illustrating an example of the distance between the reference point and the reference line and the preset distance information according to the embodiment of the present invention.
Figure 11B:
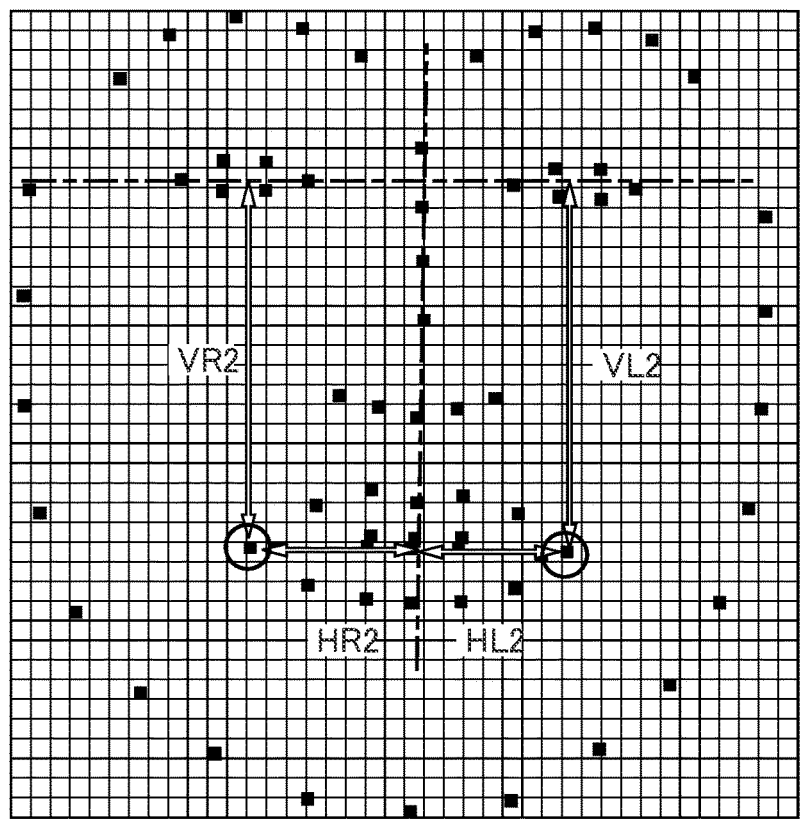

Then, when the fingers move in the directions (2) as shown in FIG. 11A, VR1 changes to VR2, VL1 to VL2, HR1 to HR2, and HL1 to HL2 as shown in FIG. 11B. The changed distances are compared to the pieces of distance information. In the example shown in FIG. 11B, VR0≤VR2, VL0≤VL2, HR0<HR2, and HL0<HL2 are met.

Figure 12A:
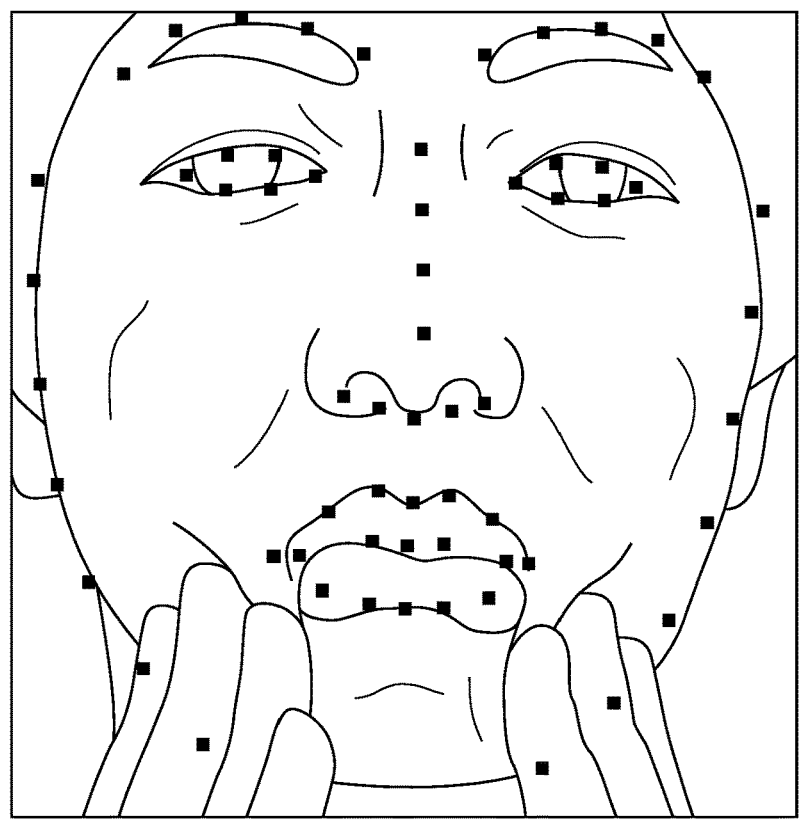
FIGS. 12A and 12B are diagrams illustrating an example of the distance between the reference point and the reference line and the preset distance information according to the embodiment of the present invention.
Figure 12B:
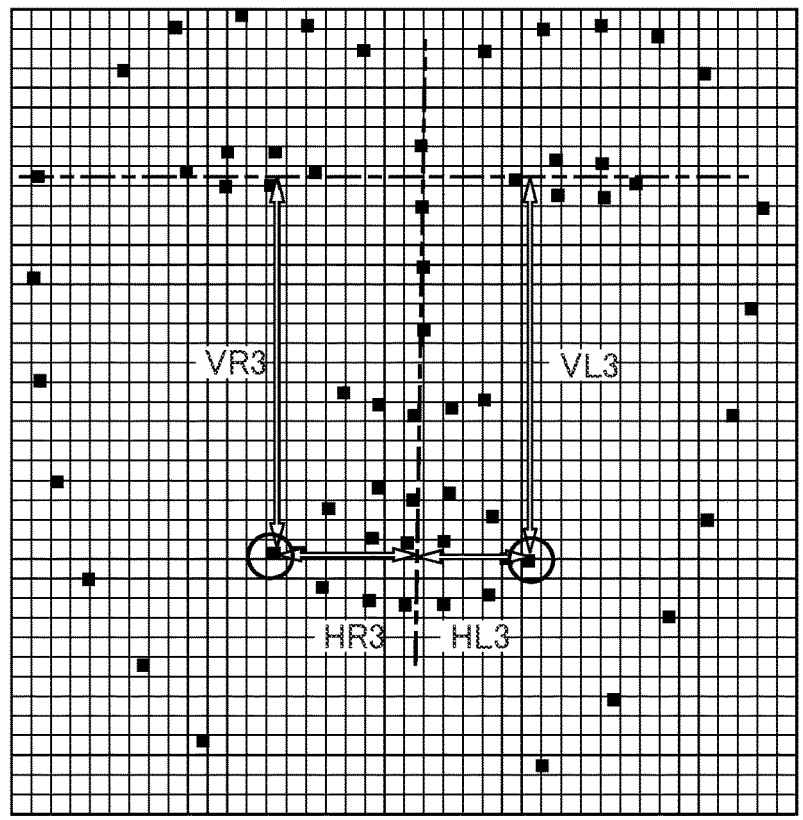
Figure 13A:
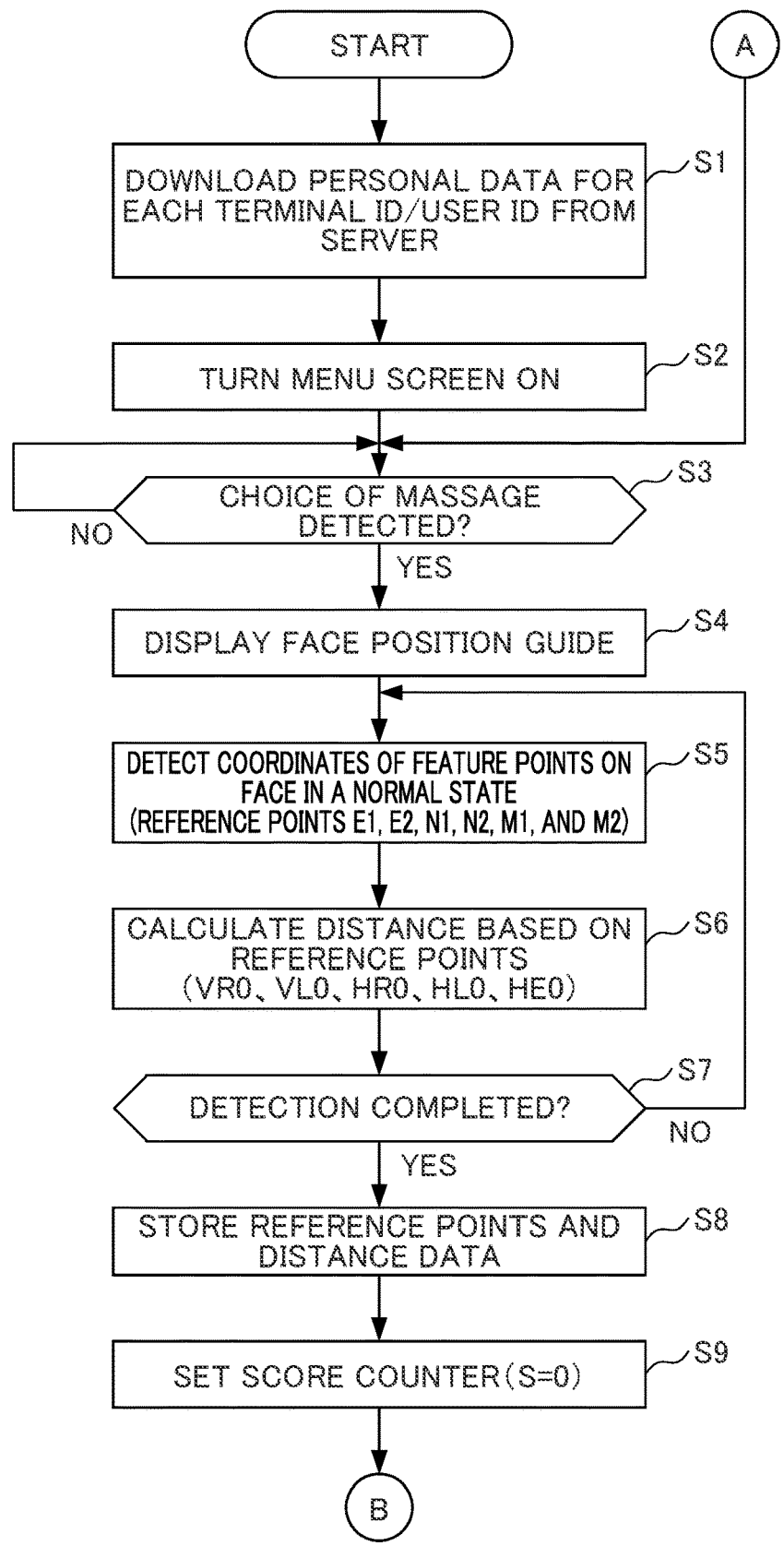
FIG. 13A is a flowchart of operation of the image processing device according to the embodiment of the present invention.
Figure 13B:
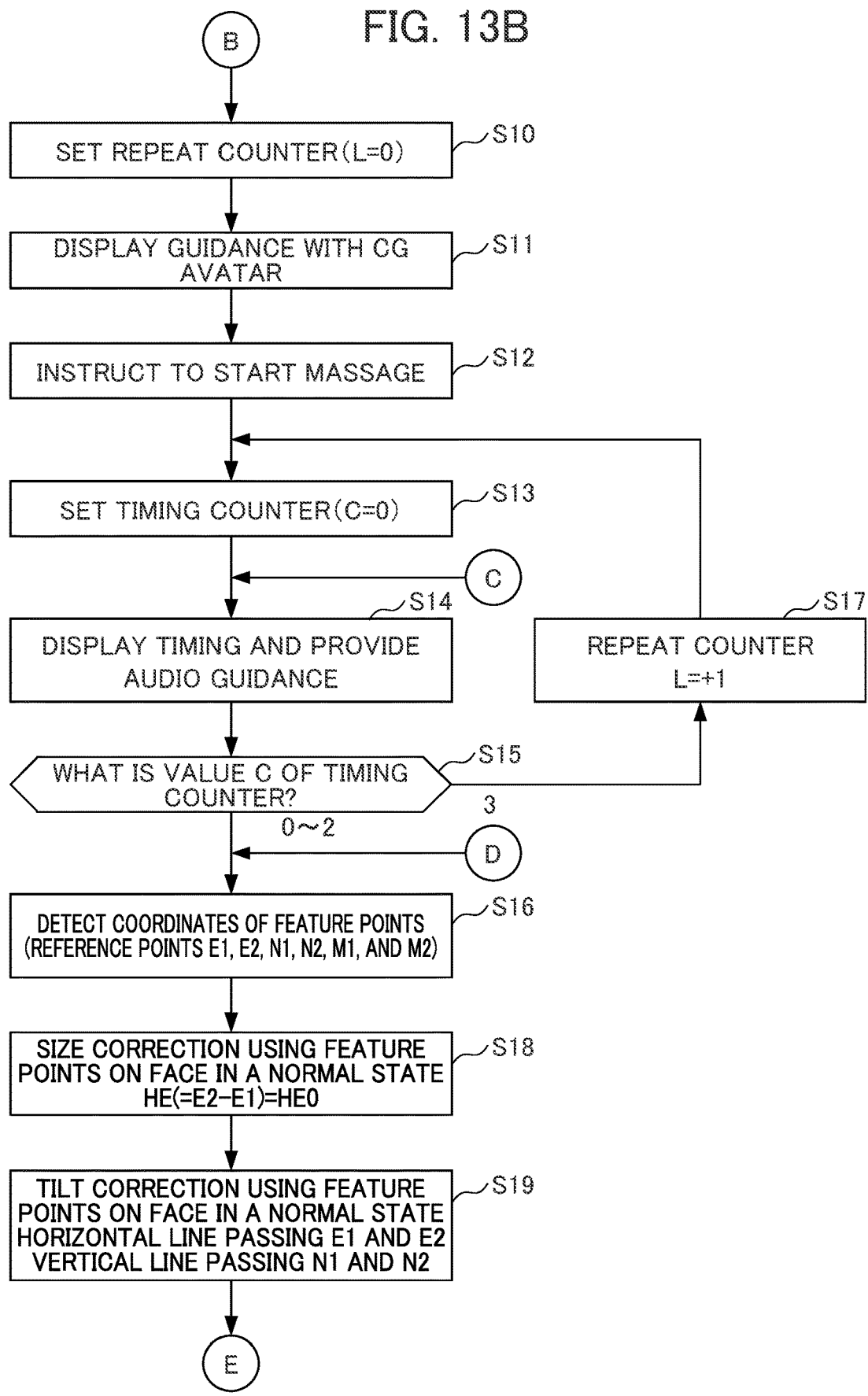
FIG. 13B is a flowchart of operation of the image processing device according to the embodiment of the present inventions
Figure 13C:
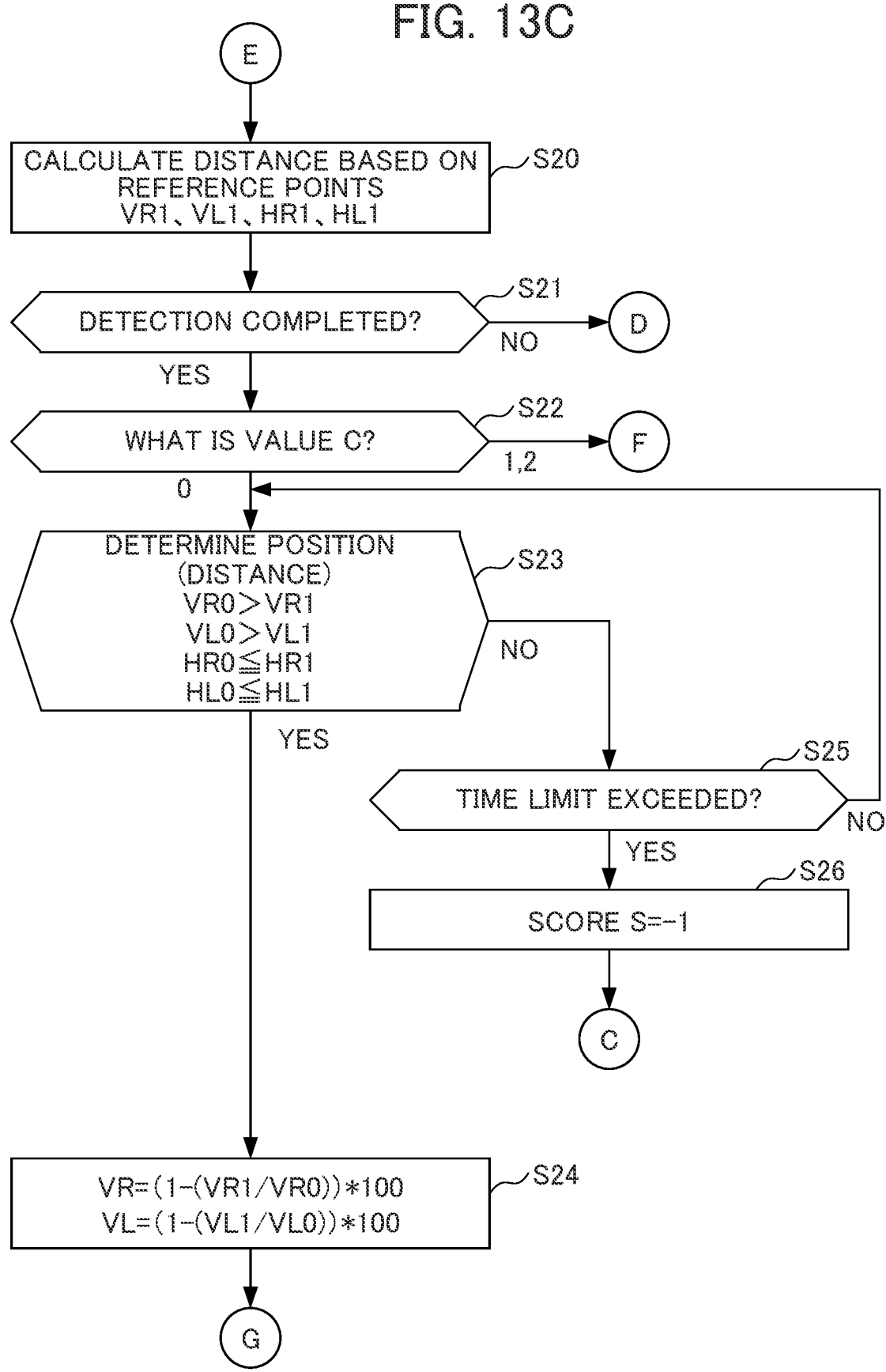
FIG. 13D is a flowchart of operation of the image processing device according to the embodiment of the present invention.
FIG. 13E is a flowchart of operation of the image processing device according to the embodiment of the present invention.
FIG. 13F is a flowchart of operation of the image processing device according to the embodiment of the present invention.
Figure 13D:
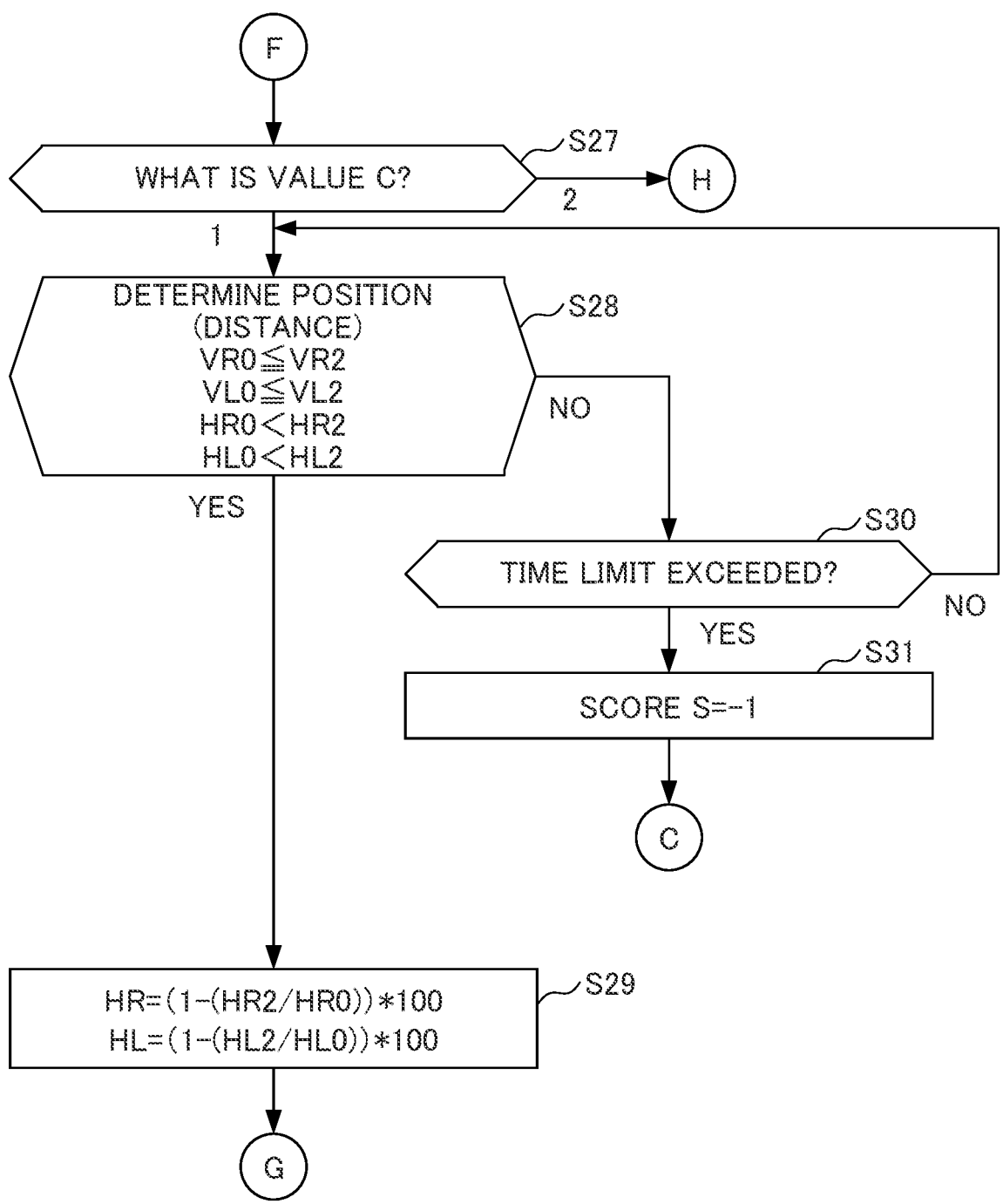
Figure 13E:
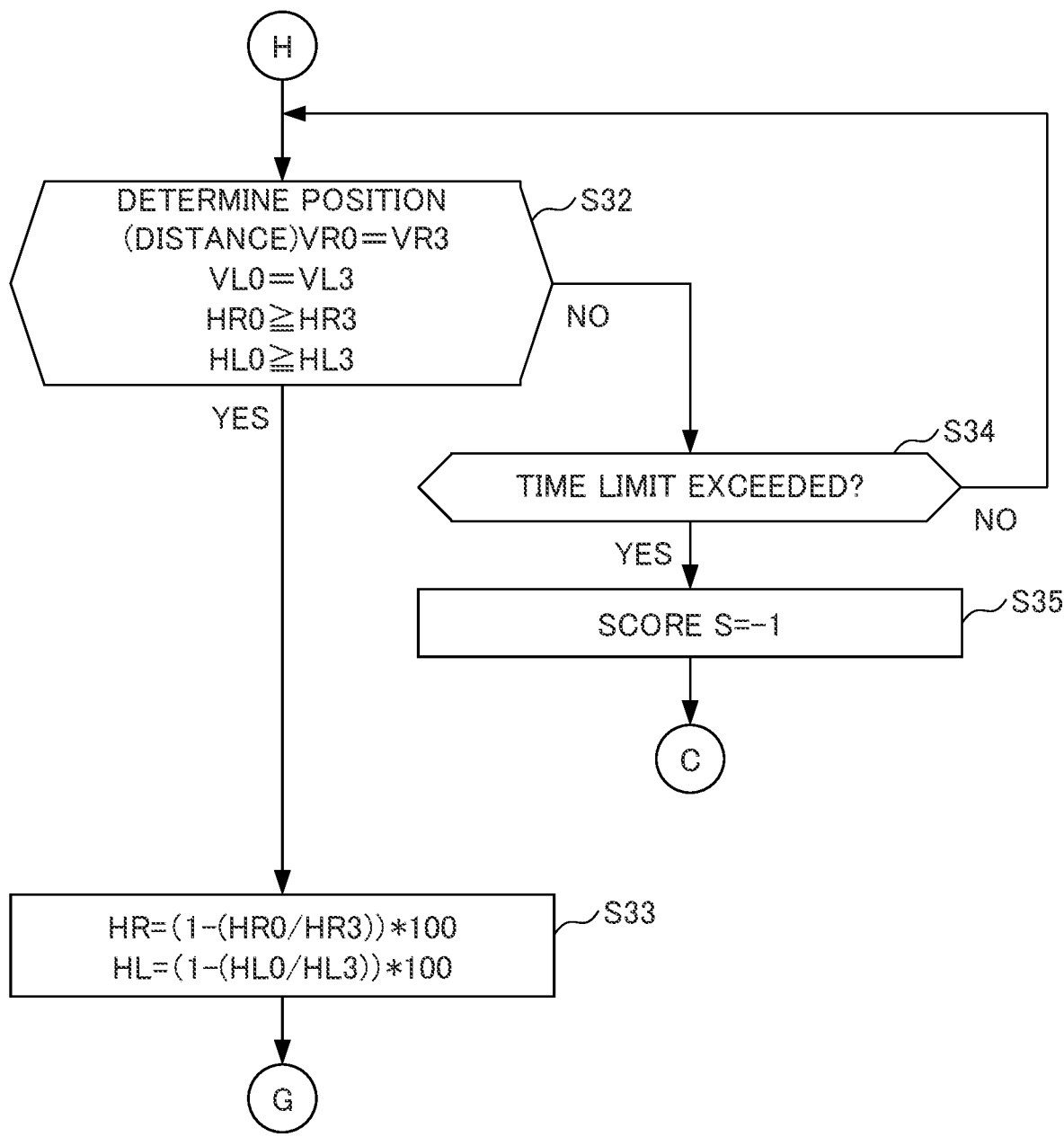
Figure 13F:
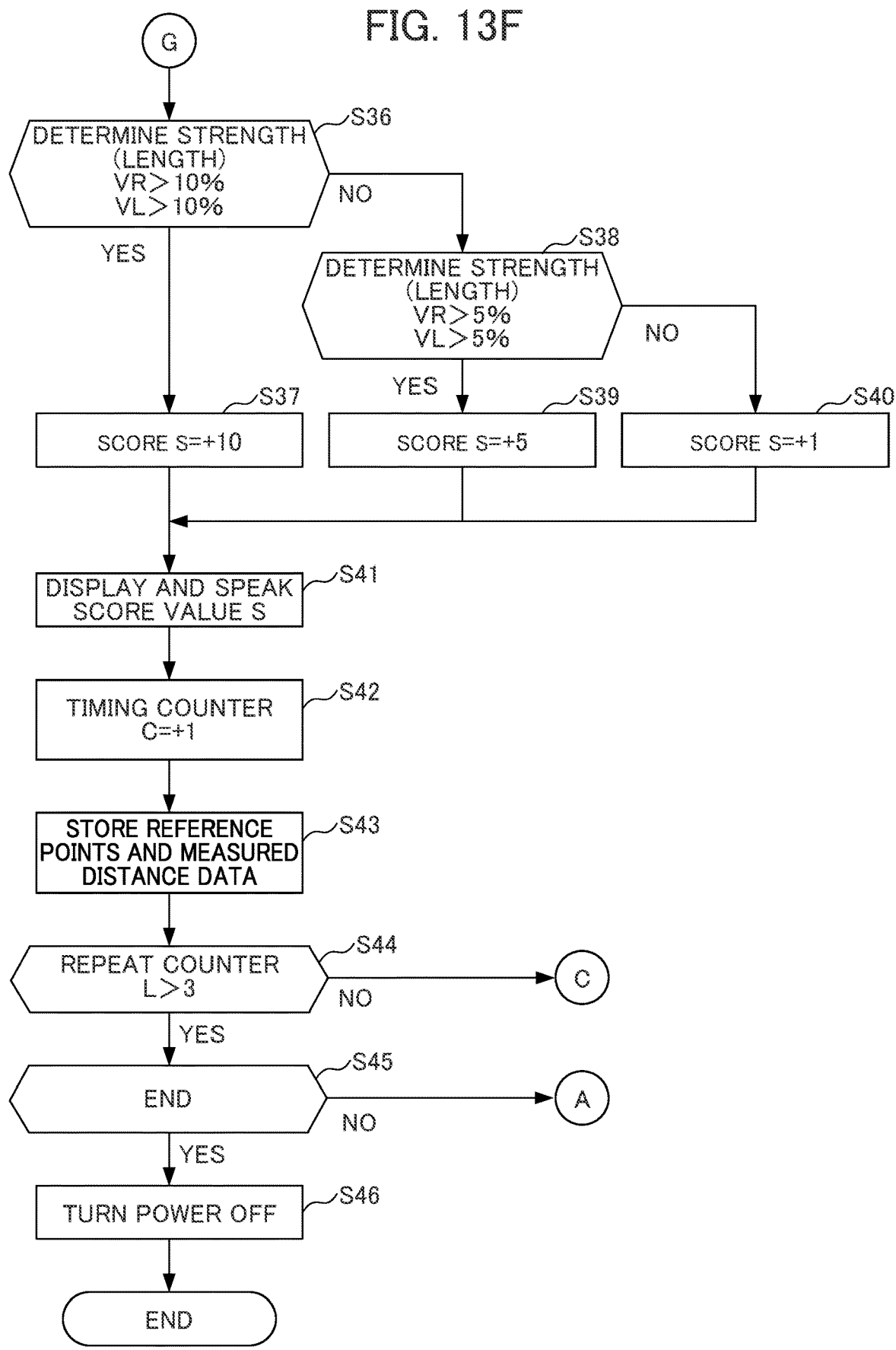

Finally, when the fingers move in the directions (3) as shown in FIG. 12A, VR2 changes to VR3, VL2 to VL3, HR2 to HR3, and HL2 to as shown in FIG. 12B. The changed distances are compared to the pieces of distance information. In the example shown in FIG. 12B, VR0=VR3, VL0=VL3, HR0≥HR3, and HL0≥HL3 are met. Regarding the movement of the feature points, the determination of "=", "≤", and "≥" does not indicate that the positions of the feature points are strictly the same, and takes a certain degree of errors into consideration.

The evaluation unit 116 evaluates the results of comparison by the comparison unit 115, and generates an evaluation result. For example, the evaluation unit 116 may generate the evaluation result based on the degree of coincidence between the locus obtained as a result of the tracking of the movement of the feature points and the preset locus information. The evaluation unit 116 may generate the evaluation result based on the degree of coincidence between the timing of the movement of the feature points and the preset timing information. The evaluation unit 116 may generate the evaluation result based on the degree of coincidence between the distance between the plurality of feature points detected and the distance information. The evaluation unit 116 may store these evaluation results in the evaluation result information storage 194, and may generate another evaluation result based on the history of the evaluation results stored in the evaluation result information storage 194.

The display control unit 117 serving as an output means executes processing to output the comparison results, the evaluation results, and the history of the evaluation results to the display 18. In the following description, the display control unit 117 may be sometimes referred to as an "output unit 117".

The display control unit 117 also executes processing for switching between a first display mode and a second display mode. In the first display mode, an image of the user is displayed as a primary image, together with a secondary image which is a composite image of an avatar image and a guiding image. In the second display mode, the image of the user is displayed as a secondary image, together with the composite image of the avatar image and the guiding image as the primary image. As shown in FIG. 2, the composite image of the avatar image and the guiding image can be shown in a large size in the center of the screen as the primary image, together with the image of the user shown in a smaller size than the primary image in a lower portion of the screen as the secondary image. Conversely, the image of the user can be shown in a large size in the center of the screen as the primary image, together with the composite image of the avatar image and the guiding image shown in a smaller size than the primary image in a lower portion of the screen as the secondary image.

The display control unit 117 may automatically show, as an image or text, a direction to which the user is supposed to turn the face, how to massage, and the biometric information in a region not overlapping with a mirror image of the user's face or the face of the avatar image during a series of guidance. The display control unit 117 may output the guidance information by a different method together with the displayed information. For example, the display control unit 117 may read guidance information including sound data, and may output sound or music generated from the read guidance information. The display control unit. 117 may change, for example, the state of lighting by the light emitter.

[Image Processing]

FIGS. 13A to 13F are flowcharts illustrating an example of an overall flow of first image processing executed by the image processing device 1 of FIG. 1 having the functional configuration shown in FIG. 5.

In Step S1, the setting processing unit 111 performs initial setting. For example, the setting processing unit 111 downloads personal data which is set for each user ID from the authentication server included in the server group 3.

In Step S2, the setting processing unit 111 executes start processing to display a menu screen on the display 18.

If the user chooses the massage and the choice is detected in Step S3 (the answer is YES in S3), the process proceeds to Step S4. If the user does not choose the massage yet and no choice is detected (the answer is NO in S3), the process repeats Step S3.

In Step S4, the display control unit 117 allows the display 18 to show a "face position guide" with which the user aligns the face to do the massage.

In Step S5, the detection unit 113 detects the coordinates of the feature points on the face in a normal state (including the reference points E1, E2, N1, N2, M1, and M2 in the example described above).

In Step S6, the comparison unit 115 calculates a distance between each of the reference points and an associated one of the reference lines (VR0, VL0, HR0, HL0, and HE0 in the example described above).

In Step S7, if the detection of the feature points is completed (the answer is YES in S7), the process proceeds to Step S8. If the detection of the feature points is not completed (the answer is NO in Step S7), the process proceeds to Step S5.

In Step S8, the comparison unit 115 stores the coordinates of the reference points detected in Step S5 and data of the distances associated with the reference points calculated in Step S6 in the actual measurement information storage 193.

In Step S9, the setting processing unit 111 sets a score value S, which is the evaluation result and counted by a score counter, to zero.

In Step S10, the setting processing unit 111 sets a repeat count value L, which is a repeat count of the massage and counted by a repeat counter, to zero.

In Step S11, the display control unit 117 displays guidance of the massage with a CG avatar.

In Step S12, the display control unit 117 displays an instruction to start the massage to the user.

In Step S13, the setting processing unit 111 sets timing values (C) in the whole massage. Specifically, the timing value after the massage of FIG. 10A is set to C=1, the timing value after the massage of FIG. 11A to C=2, and the timing value after the massage of FIG. 12A to C=3. At present, the timing value counted by the timing counter is set to zero because the massage is not started yet.

In Step S14, the display control unit 117 displays the timing of the massage on the display 18, and provides audio guidance from a speaking unit (not shown).

In Step S15, if the timing value C counted by the timing counter is any one of zero to two (the answer is zero to two in S15), the process proceeds to Step S16. If the timing value C is three (the answer is three in S15), the process proceeds to Step S17.

In Step S16, the detection unit 113 detects the coordinates of the feature points (reference points E1, E2, N1, N2, M1, and M2 in the example described above).

In Step S17, one is added to the repeat count value L counted by the repeat counter. Thereafter, the process proceeds to Step S13.

In Step S18, the correction unit 114 corrects the size of a set of the feature points using the reference points on the face in the normal state. In this case, the correction is made so that the distance HE (=E2−E1) becomes HE0 in the normal state.

In Step S19, the correction unit 114 corrects the tilt of the set of the feature points using the reference points on the face in the normal state. More specifically, the correction unit. 114 makes a correction so that the horizontal line passing E1 and E2 is level and the vertical line passing N1 and N2 is plumb.

In Step S20, the comparison unit 115 calculates a distance related to each of the reference points (VR1, VL1, HR1, and HL1 in the example described above).

In Step S21, if the detection by the detection unit 113 is completed (the answer is YES in S21), the process proceeds to Step S22. If the detection is not completed (the answer is NO in S21), the process proceeds to Step S16.

In Step S22, the value C is detected. If C=0, (the answer is zero in S22), the process proceeds to Step S23. If the value is other than zero, e.g., C is any one of one or two (the answer is one or two in S22), the process proceeds to Step S27.

In Step S23, the treatment in the direction (1) shown in FIG. 9A is performed. If the positions of the feature points VR0, VL0, HR0, and HL0 are shifted to meet VR0>VR1, VL0>VL1, HR0≤HR1, and HL0≤HL1 (the answer is YES in S23), the process proceeds to Step S24. Otherwise (the answer is NO in S23), the process proceeds to Step S25.

In Step S24, the comparison unit 115 calculates the rate of change VR from VR0 to VR1 and the rate of change VL from VL0 to VL1 from the formulae (1) and (2).

$$VR=(1-(VR1/VR0))*100 \quad (1)$$

$$VL=(1-(VL1/VL0))*100 \quad (2)$$

Thereafter, the process proceeds to Step S36.

In Step S25, if the treatment in the direction (1) shown in FIG. 9A goes on beyond a predetermined time limit (the answer is YES in S25), the process proceeds to Step S26. If the treatment ends before the time limit (the answer is NO in S25), the process proceeds to Step 23.

In Step S26, the evaluation unit 116 subtracts one from the score value S which is the evaluation result. Thereafter, the process proceeds to Step S14.

In Step S27, if the value C is one, (the answer is one in S27), the process proceeds to Step S28. If the value C is two, (the answer is two in S27), the process proceeds to Step S32.

In Step S28, the treatment in the directions (2) shown in FIG. performed. If the positions of the feature points VR0, VL0, HR0, and HL0 are shifted to meet VR0≤VR2, VL0≤VL2, HR0<HR2, and HL0<HL2 (the answer is YES in S28), the process proceeds to Step S29. Otherwise (the answer is NO in S28), the process proceeds to Step S30.

In Step S29, the comparison unit 115 calculates the rate of change HR from HR0 to HR2 and the rate of change HL from HL0 to HL2 from the formulae (3) and (4).

$$HR=(1-(HR2/HR0))*100 \quad (3)$$

$$HL=(1-(HL2/HL0))*100 \quad (4)$$

Thereafter, the process proceeds to Step S36.

In Step S30, if the treatment in the directions (2) shown in FIG. 9A goes on beyond a predetermined time limit (the answer is YES in S30), the process proceeds to Step S31. If the treatment ends before the time limit (the answer is NO in S30), the process proceeds to Step S28.

In Step S31, the evaluation unit 116 subtracts one from the score value S which is the evaluation result. Thereafter, the process proceeds to Step S14.

In Step S32, the treatment in the directions (3) shown in FIG. 9A is performed. If the positions of the feature points VR0, VL0, HR0, and HL0 are shifted to meet VR0=VR3, VL0=VL3, HR0≥HR3, and HL0≥HL3 (the answer is YES in S32), the process proceeds to Step S33. Otherwise (the answer is NO in S32), the process proceeds to Step S34.

In Step S33, the comparison unit 115 calculates the rate of change HR from HR3 to HR0 and the rate of change HL from HL3 to HL0 from the formulae (5) and (6).

$$HR=(1-(HR0/HR3))*100 \qquad (3)$$

$$HL=(1-(HL0/HL3))*100 \qquad (4)$$

Thereafter, the process proceeds to Step S36.

In Step S34, if the treatment in the directions (3) shown in FIG. 9A goes on beyond a predetermined time limit (the answer is YES in S34), the process proceeds to Step S35. If the treatment ends before the time limit (the answer is NO in S34), the process proceeds to Step S32.

In Step S35, the evaluation unit 116 subtracts one from the score value S which is the evaluation result. Thereafter, the process proceeds to Step S14.

If VR>10% and VL>10% are met in Step S36 (the answer is YES in S36), the process proceeds to Step S37. Otherwise (the answer is NO in S36), the process proceeds to Step S38.

In Step S37, the evaluation unit 116 adds 10 to the score value S which is the evaluation result. Thereafter, the process proceeds to Step S41.

If VR>5% and VL>5% are met in Step S38 (the answer is YES in S38), the process proceeds to Step S39. Otherwise (the answer is NO in S38), the process proceeds to Step S40.

In Step S39, the evaluation unit 116 adds five to the score value S which is the evaluation result. Thereafter, the process proceeds to Step S41.

In Step S40, the evaluation unit 116 adds one to the score value S which is the evaluation result. Thereafter, the process proceeds to Step S41.

In Step S41, the display control unit 117 displays the score value S, and the speaking unit (not shown) speaks the score value S.

In Step S42, the setting processing unit 111 adds one to the timing value C counted by the timing counter.

In Step S43, the comparison unit 115 stores the coordinates of the reference points and data of the measurements of the distances associated with the reference points in the actual measurement information storage 193.

If the repeat count value L counted by the repeat counter exceeds three in Step S44 (the answer is YES in S44), the process proceeds to Step S45. If the repeat count value L does not exceed three (the answer is NO in S44), the process proceeds to Step S14.

If the massage ends in Step S45 (the answer is YES in S45), the process proceeds to Step S46. Otherwise (the answer is NO in S45), the process proceeds to Step S3.

In Step S46, the image processing device 1 turns the power OFF.

Figure 14A:
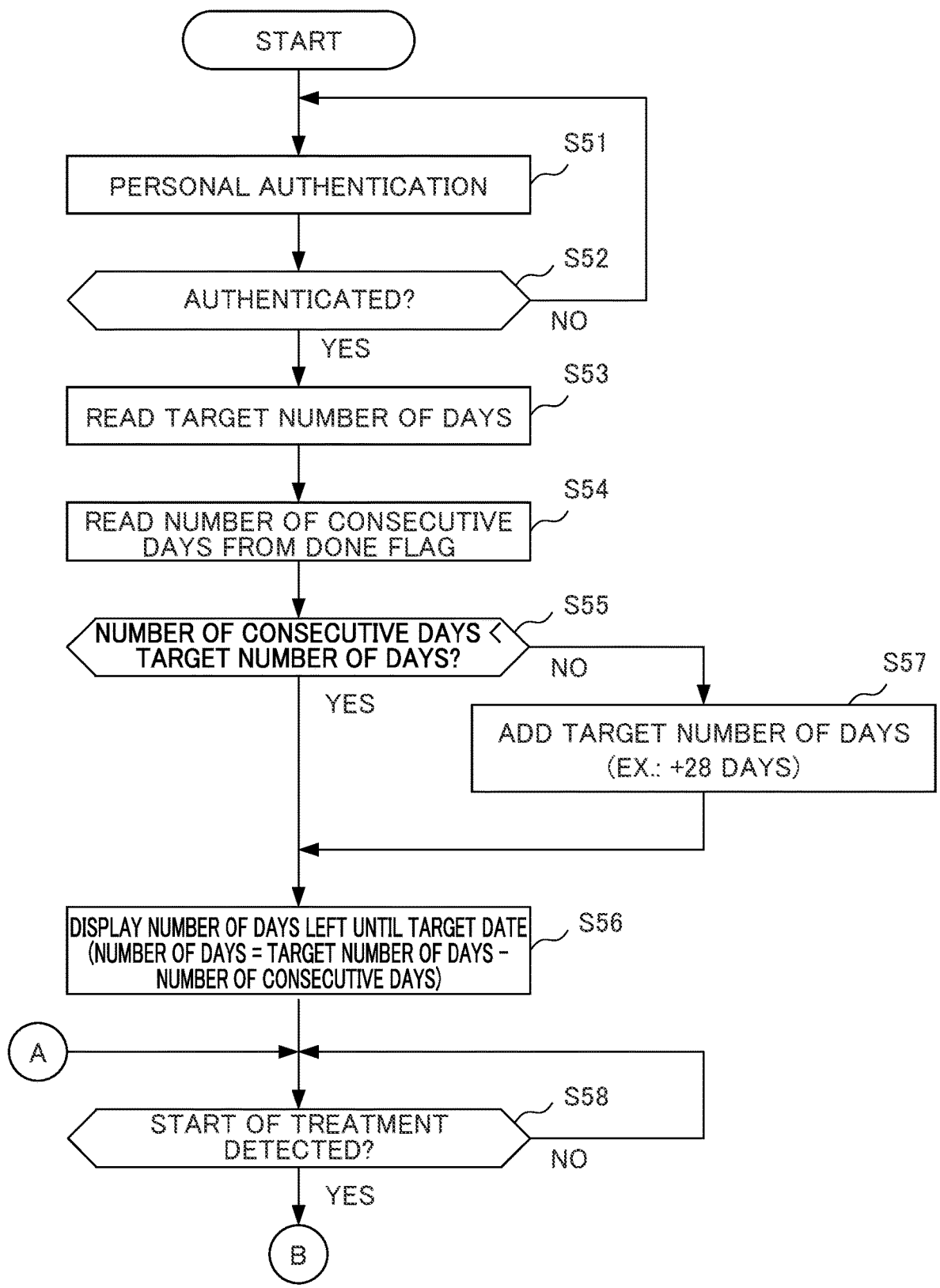
FIG. 14A is a flowchart of operation of the image processing device according to the embodiment of the present invention.
Figure 14B:
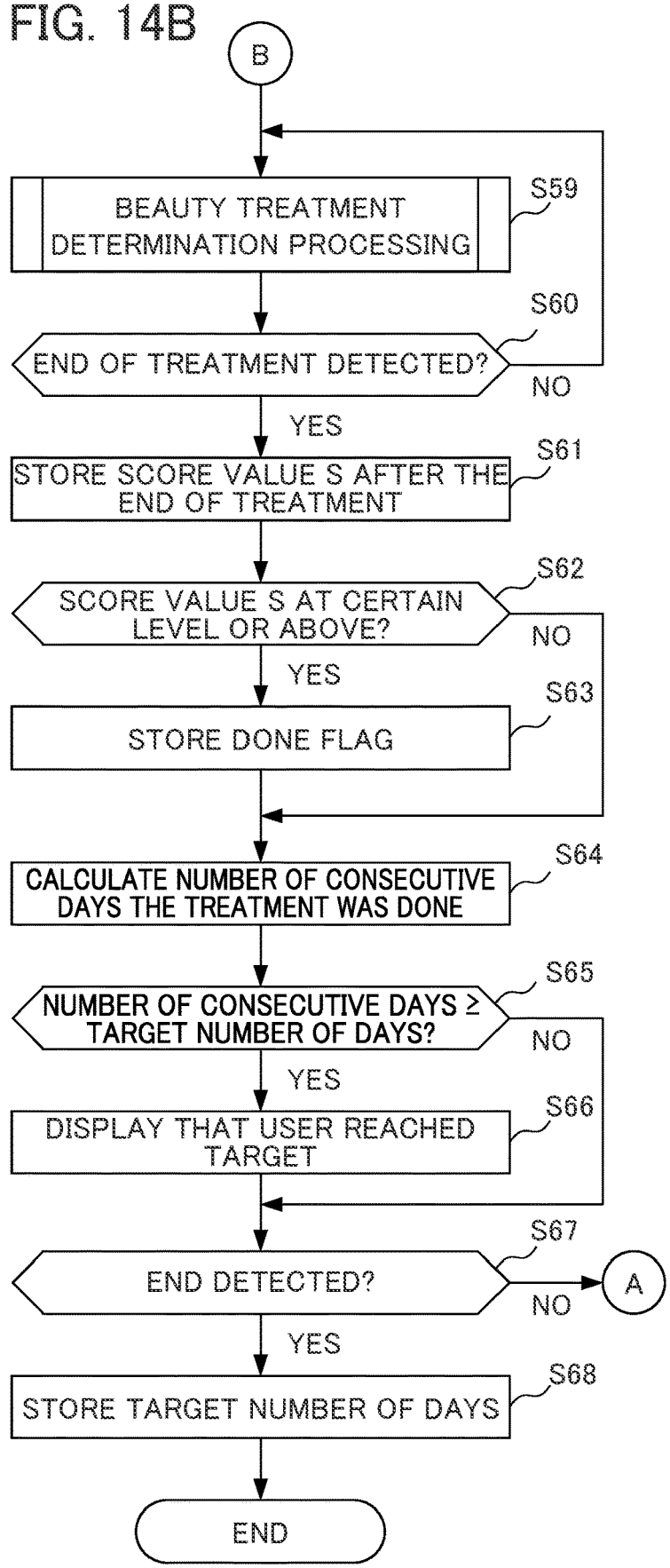
FIG. 14B is a flowchart of operation of the image processing device according to the embodiment of the present invention.

FIGS. 14A and 14B are flowcharts illustrating an example of an overall flow of second image processing executed by the image processing device 1 of FIG. 1 having the functional configuration shown in FIG. 5. The second image processing is executed when the user does the massage for a long period of time.

In Step S51, the setting processing unit 111 queries the server group 3 to perform personal authentication of the user.

If the user is authenticated in Step S52 (the answer is YES in S52), the process proceeds to Step S53. If the user is not authenticated (the answer is NO in S52), the process proceeds to Step S51.

In Step S53, the setting processing unit 111 reads the target number of days the user tries to do the massage in succession from the server group 3.

In Step S54, the setting processing unit 111 reads the number of consecutive days the user did the massage in succession from the server group 3 based on a done flag which is a flag added to the history of the actual measurement data and indicates whether the massage is done.

If the number of consecutive days is less than the target number of days in Step S55 (the answer is YES in S55), the process proceeds to Step S56. If the number of consecutive days reaches or exceeds the target number of days (the answer is NO in S55), the process proceeds to Step S57.

In Step S56, the display control unit 117 shows on the display 18 the number of days left until the target date, i.e., the number of days obtained by subtracting the number of consecutive days from the target number of days.

In Step S57, the setting processing unit 111 adds the target number of days. For example, the setting processing unit 111 adds 28 days, i.e., four weeks, to the target number of days at present.

If the start of the treatment is detected in Step S58 (t answer is YES in S58), process proceeds to Step S59. If the start of the treatment is not detected (the answer is NO in S58), the process proceeds to Step S58.

In Step S59, the image processing device 1 executes the processing of Steps S1 to S46 shown in FIGS. 13A to 13F as beauty treatment determination processing.

If the end of the treatment is detected in Step S60 (the answer is YES in S60), the process proceeds to Step S61. If the end of the treatment is not detected (the answer is NO in S60), the process proceeds to Step S59.

In Step S61, the evaluation unit 116 stores the score value after the end of the treatment in the evaluation result information storage 194.

If this score value S is at a certain level or above in Step S62 (the answer is YES in S62), the process proceeds to Step S63. If this score value S falls below the certain level (the answer is NO in S62), the process proceeds to Step S64.

In Step S63, the setting processing unit 111 stores a flag indicating that the treatment that has brought the score value S to a certain level or above is done in the server group 3.

In Step S64, the setting processing unit 111 calculates the number of consecutive days the treatment was done.

If the number of consecutive days reaches or exceeds the target number of days in Step S65 (the answer is YES in S65), the process proceeds to Step S66. If the number of consecutive days is less than the target number of days (the answer is NO in S65), the process proceeds to Step S67.

In Step S66, the display control unit 117 displays on the display 18 that the user reached the target.

If the end of the treatment is detected in Step S67 (the answer is YES in S67), the process proceeds to Step S68. If the end of the treatment is not detected (the answer is N1 in S67), the process proceeds to Step S58.

In Step S68, the setting processing unit 111 stores the target number of days in the server group 3.

The image processing device 1 of the present embodiment described above includes the acquisition unit 112, the detection unit 113, the comparison unit 115, and the output unit. (display control unit) 117. The acquisition unit 112 acquires the image taken of the object. The detection unit 113 detects the feature points in a real image of the object included in the image taken of the target. The comparison unit. 115 compares the locus obtained as a result of the tracking of the movement of the feature points in the real image included in the image of the object acquired by the acquisition unit 112 with the preset locus information to acquire the comparison result. The output unit 117 outputs the comparison result.

The comparison between the locus of the movement of the feature points of the object detected using a camera and the preset locus information allows determination of whether the treatment is correctly given to the object.

The detection unit 113 detects a plurality of feature points. The comparison unit 115 obtains a distance between the plurality of feature points detected, and compares the distance with the preset distance information. Thus, how much the distance between the feature points has changed from the initial set value can be acquired, and whether the treatment is correctly given to the object can be determined based on the acquired result.

The image is taken while the treatment is given to the object. The distance information is information about the distance that varies depending on partial change in shape of the object caused by the treatment. Thus, whether the treatment is correctly given can be determined based on how the shape of the object is changed by the treatment.

The image processing device 1 of the present embodiment further includes the evaluation unit 116. The evaluation unit 116 evaluates the comparison result obtained by the comparison unit. 115, and generates an evaluation result. The output unit 117 further outputs the evaluation result. Thus, how correctly the treatment is given can be expressed as a score based on the change of the feature points.

The evaluation unit 116 evaluates the degree of coincidence between the distance and the distance information. Thus, now correctly the treatment is given can be expressed as a score based on how much the distance between the feature points coincides with the preset distance information.

The image processing device 1 of the present embodiment further includes the evaluation result information storage 194. The evaluation result information storage 194 stores the history of the evaluation result. The output unit 117 outputs the history of the evaluation result stored in the evaluation result information storage 194. This allows the user of the image processing device 1 to thoroughly know the history of the evaluation result, i.e., the history of the score representing how correctly the treatment has been given so far.

When the number of consecutive days the treatment is evaluated to be at the certain level or above by the evaluation unit 116 reaches or exceeds the preset target number of days, the output unit 117 outputs that the number of consecutive days has reached or exceeded the target number of days. This motivates the user of the image processing device 1 to continue the treatment that is evaluated to be at the certain level or above.

The comparison unit 115 compares the timing of the movement with the preset timing information. This allows the user of the image processing device 1 to thoroughly know whether the treatment is done at a suitable timing.

The object is an organ of a human. Thus, whether the treatment such as a massage is correctly given to the organ of the human can be determined.

Alternatively, the object is a face of a human. Thus, whether the treatment such as a massage is correctly given to the face of the human can be determined.

[Variations]

The present invention is not limited to the embodiment described above. Modifications and improvements within the scope that the object of the present invention can be achieved are included in the present invention. For example, the above-described embodiment can be modified as follows.

It has been described in the embodiment that the rate of change of the distance between the feature points is compared with a predetermined value, and how correctly the treatment is given is expressed as a score based on the comparison result. However, the comparison is not limited to this example. For example, the length of the distance between the feature points changed may be compared with a predetermined value, and how correctly the treatment is given may be expressed as a score based on the comparison result.

The image processing device 1 of the embodiment may have the display 18 combined with a mirror having a reflective surface. In this case, the mirror is comprised of a half mirror having optical properties, including both of transparency and reflectivity. The mirror is superposed on the front side of the display 18 in the direction of the user's sight. This arrangement allows the user to see, for example, the face of the user reflected in the mirror instead of the image of the user taken by the imaging unit 16, together with various types of information (e.g., a composite image) that are shown on the display 18 and penetrate the mirror. Specifically, in the above-described embodiment, the user sees the image of the user, who is the subject, taken by the imaging unit 16 as a real image of the user. However, in this variation, the user sees a mirror image of the user reflected in the mirror as the real image of the user. This configuration can provide the same advantages as the embodiment.

Other Modified Examples

For example, in the above embodiment, it is assumed that the image processing device 1 cooperates with the respective servers included in the server group 3, but the functions of the respective servers may be added to the image processing device 1, and all the processes may be performed only in the image processing device 1.

In addition, in the above embodiment, the image processing device 1 to which the present invention is applied has been described by way of example of an electronic device incorporated in a portable self-standing mirror, but the present invention is not particularly limited thereto. For example, the present invention can be applied to an electronic device incorporated into a large mirror such as a full-length mirror, an electronic device incorporated into a stationary bathroom vanity, and a mirror-shaped electronic device installed in a bathroom.

The processing sequence described above can be executed by hardware, and can also be executed by software. In other words, the functional configuration of FIG. 5 is merely an illustrative example, and the present invention is not particularly limited thereto. More specifically, the types of functional blocks employed to realize the above-described functions are not particularly limited to the examples shown in FIG. 7, so long as the image processing device 1 can be provided with the functions enabling the aforementioned processing sequence to be executed in its entirety.

In addition, a single functional block may be configured by a single piece of hardware, a single installation of software, or a combination thereof. The functional configurations of the present embodiment are realized by a processor executing arithmetic processing, and processors that can be used for the present embodiment include a unit configured by a single unit of a variety of single processing devices such as a single processor, multi-processor, multi-core processor, etc., and a unit in which the variety of processing devices are combined with a processing circuit such as ASIC (Application Specific integrated Circuit) or FPGA (Field-Programmable Gate Array).

In the case of having the series of processing executed by software, the program constituting this software is installed from a network or recording medium to a computer or the like. The computer may be a computer equipped with dedicated hardware. In addition, the computer may be a computer capable of executing various functions, e.g., a general purpose personal computer, by installing various programs.

The storage medium containing such a program can not only be constituted by the removable medium 100 of FIG. 4 distributed separately from the device main body for supplying the program to a user, but also can be constituted by a storage medium or the like supplied to the user in a state incorporated in the device main body in advance. The removable medium 100 is composed of, for example, a magnetic disk (including a floppy disk), an optical disk, a magnetic optical disk, or the like. The optical disk is composed of, for example, a CD-ROM (Compact Disk-Read Only Memory), a DVD (Digital Versatile Disk), Blu-ray (Registered Trademark) or the like. The magnetic optical disk is composed of an MD (Mini-Disk) or the like. The storage medium supplied to the user in a state incorporated in the device main body in advance is constituted by, for example, the ROM 12 of FIG. 4 in which the program is recorded or a hard disk included in the storage unit 19 of FIG. 4 or 5, etc.

It should be noted that, in the present specification, the steps defining the program recorded in the storage medium include not only the processing executed in a time series following this order, but also processing executed in parallel or individually, which is not necessarily executed in a time series. Further, in the present specification, the terminology of the system means an entire apparatus including a plurality of apparatuses and a plurality of units.

The embodiments of the present invention described above are only illustrative, and are not to limit the technical scope of the present invention. The present invention can assume various other embodiments. Additionally, it is possible to make various modifications thereto such as omissions or replacements within a scope not departing from the spirit of the present invention. These embodiments or modifications thereof are within the scope and the spirit of the invention described in the present specification, and within the scope of the invention recited in the claims and equivalents thereof.

INDUSTRIAL APPLICABILITY

The present invention is particularly useful for checking whether a beauty treatment is correctly given during the beauty treatment, and/or quantitatively evaluating the effect of the beauty treatment.

EXPLANATION OF REFERENCE NUMERALS

1 Measurement Device
2 Network
3 Server Group
11 CPU
12 ROM
13 RAM
14 Bus
15 Input/Output. Interface
16 Imaging Unit
17 Input Unit
18 Display
19 Storage
20 Communication Unit
21 Drive
30 Body
31 Leg
32 Hinge
100 Removable Media
111 Setting Processing Unit
112 Acquisition Unit
113 Detection Unit
114 Correction Unit
115 Comparison Unit
116 Evaluation Unit
117 Display Control Unit
S Image Processing System

The invention claimed is:

1. An image processing device comprising:
at least one camera;
an input/output interface; and
at least one processor,
wherein the at least one processor executes operations including:
detecting feature points in a facial image of an object included in an image taken by the camera;
setting, from among the feature points, reference points and reference lines which are used as a reference for detecting movement of the feature points for different beauty treatments;
performing image processing to correct a positional relationship among the feature points, based on a comparison of a distance between the reference points with a preset reference distance between the reference points, and a tilt of the reference lines relative to each of horizontal and vertical lines;
generating an evaluation result based on a degree of coincidence between a distance between the feature points and distance information, wherein the distance between the feature points indicates the distance between the feature points in a state in which the object varies depending on a partial change in shape of the object caused by the beauty treatment, and the distance information is information about an ideal distance between the feature points in the state in which the object varies depending on the partial change in shape of the object caused by the beauty treatment;
generating a guiding image which indicates an ideal position or an ideal direction of the movement of the feature points, based on the evaluation result; and
outputting a composite image on the input/output interface, wherein the composite image is obtained by combining the guiding image with an avatar image which is an alternative image of the object.

2. The image processing device according to claim 1, wherein the at least one processor executes operations further comprising:
outputting a facial image of the object taken by the camera on the input/output interface.

3. The image processing device according to claim 2, wherein the at least one processor executes operations further comprising:
outputting the facial image of the object on a display region not overlapping with the composite image on the input/output interface.

4. The image processing device according to claim 3, wherein the at least one processor executes operations further comprising:

outputting guidance information on a display region not overlapping with the facial image or the composite image on the input/output interface.

5. The image processing device according to claim 4, wherein the at least one processor executes operations further comprising:
generating an evaluation result in which the beauty treatment is expressed as a score based on determined results, and outputting the evaluation result.

6. The image processing device according to claim 5, further comprising:
a memory that stores a history of the evaluation result, wherein the at least one processor executes operations further comprising:
storing a history of the evaluation result in the memory, and outputting the history stored in the memory.

7. An image processing method executed by a computer, the method comprising:
detecting feature points in a facial image of an object included in an image taken by at least one camera;
setting, from among the feature points, reference points and reference lines which are used as a reference for detecting movement of the feature points for different beauty treatments;
performing image processing to correct a positional relationship among the feature points, based on a comparison of a distance between the reference points with a preset reference distance between the reference points, and a tilt of the reference lines relative to each of horizontal and vertical lines;
generating an evaluation result based on a degree of coincidence between a distance between the feature points and distance information, wherein the distance between the feature points indicates the distance between the feature points in a state that in which the object varies depending on a partial change in shape of the object caused by the beauty treatment, and the distance information is information about an ideal distance between the feature points in the state in which the object varies depending on the partial change in shape of the object caused by the beauty treatment;
generating a guiding image which indicates an ideal position or an ideal direction of the movement of the feature points, based on the evaluation result; and
outputting a composite image on an input/output interface, wherein the composite image is obtained by combining the guiding image with an avatar image which is an alternative image of the object.

8. The image processing method according to claim 7, further comprising:
outputting a facial image of the object taken by the camera on the input/output interface.

9. The image processing method according to claim 8, further comprising:
outputting the facial image of the object on a display region not overlapping with the composite image on the input/output interface.

10. The image processing method according to claim 9, further comprising:
outputting guidance information on a display region not overlapping with the facial image or the composite image on the input/output interface.

11. A non-transitory computer-readable storage medium storing a program that is executed by a computer, the program being executable to cause the computer to perform functions comprising:
detecting feature points in a facial image of an object included in an image taken by at least one camera;
setting, from among the feature points, reference points and reference lines which are used as a reference for detecting movement of the feature points for different beauty treatments;
performing image processing to correct a positional relationship among the feature points, based on a comparison of a distance between the reference points with a preset reference distance between the reference points, and a tilt of the reference lines relative to each of horizontal and vertical lines;
generating an evaluation result based on a degree of coincidence between a distance between the feature points and distance information, wherein the distance between the feature points indicates the distance between the feature points in a state that in which the object varies depending on a partial change in shape of the object caused by the beauty treatment, and the distance information is information about an ideal distance between the feature points in the state in which the object varies depending on the partial change in shape of the object caused by the beauty treatment;
generating a guiding image which indicates an ideal position or an ideal direction of the movement of the feature points, based on the evaluation result; and
outputting a composite image on an input/output interface, wherein the composite image is obtained by combining the guiding image with an avatar image which is an alternative image of the object.

12. The non-transitory computer-readable storage medium according to claim 11, wherein the program is executable to cause the computer to perform functions further comprising:
outputting a facial image of the object taken by the camera on the input/output interface.

13. The non-transitory computer-readable storage medium according to claim 12, wherein the program is executable to cause the computer to perform functions further comprising:
outputting the facial image of the object on a display region not overlapping with the composite image on the input/output interface.

14. An image processing device comprising:
an input/output interface;
at least one camera; and
at least one processor,
wherein the at least one processor executes operations including:
detecting feature points in a facial image of an object included in an image taken by the camera;
generating a guiding image which indicates an ideal position or an ideal direction of movement of the feature points, based on a result of comparison between a result of tracking of the movement of the feature points and preset locus information; and
outputting a composite image via the input/output interface, wherein the composite image is obtained by combining the guiding image with an avatar image which is an alternative image of the object.

15. The image processing device according to claim 14, wherein the processor executes operations further comprising:
displaying a facial image of the object in display region that is different from a display region for the composite image in the input/output interface.

16. The image processing device according to claim 15, wherein the processor executes operations further comprising:

selectively executing a first display mode displaying the facial image in a center of a screen of the input/output interface and displaying the composite image in a lower portion of the screen of the input/output interface, and a second display mode displaying the facial image in the lower portion of the screen of the input/output interface and displaying the composite image in the center of the screen of the input/output interface.

17. The image processing device according to claim 14, wherein the processor executes operations further comprising:

displaying guide information in a display region that does not overlap the composite image or the facial image of the input/output interface.

* * * * *

UNITED STATES PATENT AND TRADEMARK OFFICE
CERTIFICATE OF CORRECTION

PATENT NO. : 12,315,164 B2
APPLICATION NO. : 17/762258
DATED : May 27, 2025
INVENTOR(S) : Toshihiko Otsuka and Takahiro Tomida Page 1 of 1

It is certified that error appears in the above-identified patent and that said Letters Patent is hereby corrected as shown below:

In the Claims

Column 19, Line 36, Claim 7, after "state" delete "that".

Column 20, Line 18, Claim 11, after "state" delete "that".

Signed and Sealed this
Twenty-sixth Day of August, 2025

Coke Morgan Stewart
*Acting Director of the United States Patent and Trademark Office*